(12) United States Patent
Shadduck

(10) Patent No.: US 8,016,823 B2
(45) Date of Patent: Sep. 13, 2011

(54) MEDICAL INSTRUMENT AND METHOD OF USE

(75) Inventor: John H. Shadduck, Menlo Park, CA (US)

(73) Assignee: Tsunami MedTech, LLC, Menlo Park, CA (US)

( * ) Notice: Subject to any disclaimer, the term of this patent is extended or adjusted under 35 U.S.C. 154(b) by 1310 days.

(21) Appl. No.: 11/244,329

(22) Filed: Oct. 5, 2005

(65) Prior Publication Data

US 2006/0135955 A1 Jun. 22, 2006

Related U.S. Application Data

(63) Continuation-in-part of application No. 10/681,625, filed on Oct. 7, 2003, now Pat. No. 7,674,259, and a continuation-in-part of application No. 10/346,877, filed on Jan. 18, 2003, now Pat. No. 6,911,028.

(60) Provisional application No. 60/615,900, filed on Oct. 5, 2004.

(51) Int. Cl.
*A61B 18/18* (2006.01)
(52) U.S. Cl. ............. 606/41; 606/46; 607/105; 607/107
(58) Field of Classification Search .................... 606/27, 606/28, 38–41, 45–50; 607/96, 104–107
See application file for complete search history.

(56) References Cited

U.S. PATENT DOCUMENTS

| 408,899 | A | 8/1889 | Bioch et al. |
|---|---|---|---|
| 697,181 | A | 4/1902 | Smith |
| 1,719,750 | A | 9/1927 | Bridge et al. |
| 3,818,913 | A | 6/1974 | Wallach |
| 3,880,168 | A | 4/1975 | Berman |
| 3,930,505 | A | 1/1976 | Wallach |
| 4,024,866 | A | 5/1977 | Wallach |
| 4,083,077 | A | 4/1978 | Knight et al. |
| 4,672,962 | A | 6/1987 | Hershenson |
| 4,682,596 | A | 7/1987 | Bales et al. |
| 4,748,979 | A | 6/1988 | Hershenson |
| 4,773,410 | A | 9/1988 | Blackmer et al. |

(Continued)

FOREIGN PATENT DOCUMENTS

WO    WO 00/11927    3/2000

(Continued)

OTHER PUBLICATIONS

Moulding et al., "Preliminary studies for achieving transcervical oviduct occlusion by hot water or low-pressure steam," *Advancesin Planned Parenthood*, vol. 12, No. 2; pp. 79-85, 1977.
U.S. Appl. No. 09/181,906, filed Oct. 28, 1998, in the name of Shadduck, Non-Final Rejection mailed Mar. 15, 2000.
U.S. Appl. No. 09/181,906, filed Oct. 28, 1998, in the name of Shadduck, Notice of Allowance mailed Sep. 26, 2000.
U.S. Appl. No. 09/281,493, filed Mar. 30, 1999 in the name of Shadduck, entitled "Ionothermal system and technique for dermal treatments".
U.S. Appl. No. 09/557,931, filed Apr. 22, 2000 in the name of Shadduck, entitled "Ionothermal delivery system and technique for medical procedures".
U.S. Appl. No. 09/580,767, filed May 30, 2000 in the name of Shadduck, entitled "Microjoule electrical discharge catheter for thrombolysis in stroke patients".

(Continued)

*Primary Examiner* — Roy D Gibson
(74) *Attorney, Agent, or Firm* — Levine Bagade Han LLP

(57) ABSTRACT

This invention relates to surgical instruments for applying energy to tissue using a a vapor-to-liquid phase transition which delivers large amount of energy to the targeted tissue. In one embodiment, the system is configured for volumetric removal of tissue by means of high velocity ejection of a vapor media from a first vapor port proximate to soft tissue wherein the vapor-to-liquid phase change of the media applies energy to the tissue. The system provides a second port coupled to a suction source that cooperates with the first vapor port to suction tissue debris from the targeted site.

36 Claims, 16 Drawing Sheets

U.S. PATENT DOCUMENTS

| | | | |
|---|---|---|---|
| 4,793,352 A | 12/1988 | Eichenlaub |
| 4,872,920 A | 10/1989 | Flynn et al. |
| 4,898,574 A | 2/1990 | Uchiyama et al. |
| 4,915,113 A | 4/1990 | Holman |
| 4,950,266 A | 8/1990 | Sinofsky |
| 4,985,027 A | 1/1991 | Dressel |
| 5,006,119 A | 4/1991 | Acker et al. |
| 5,011,566 A | 4/1991 | Hoffman |
| 5,084,043 A | 1/1992 | Hertzmann et al. |
| 5,102,410 A | 4/1992 | Dressel |
| 5,112,328 A | 5/1992 | Taboada et al. |
| 5,122,138 A | 6/1992 | Manwaring |
| 5,158,536 A | 10/1992 | Sekins et al. |
| 5,190,539 A | 3/1993 | Fletcher et al. |
| 5,217,459 A | 6/1993 | Kamerling |
| 5,217,465 A | 6/1993 | Steppe |
| 5,263,951 A | 11/1993 | Spears et al. |
| 5,277,696 A | 1/1994 | Hagen |
| 5,298,298 A | 3/1994 | Hoffman |
| 5,318,014 A | 6/1994 | Carter |
| 5,331,947 A | 7/1994 | Shturman |
| 5,334,190 A | 8/1994 | Seiler |
| 5,348,551 A | 9/1994 | Spears et al. |
| 5,352,512 A | 10/1994 | Hoffman |
| 5,417,686 A | 5/1995 | Peterson et al. |
| 5,424,620 A | 6/1995 | Cheon et al. |
| 5,433,708 A | 7/1995 | Nichols et al. |
| 5,433,739 A | 7/1995 | Sluijter |
| 5,462,521 A | 10/1995 | Brucker et al. |
| 5,500,012 A | 3/1996 | Brucker et al. |
| 5,503,638 A | 4/1996 | Cooper et al. |
| 5,524,620 A | 6/1996 | Rosenschein |
| 5,529,076 A | 6/1996 | Schachar |
| 5,542,928 A | 8/1996 | Evans et al. |
| 5,549,628 A | 8/1996 | Cooper et al. |
| 5,554,172 A | 9/1996 | Horner et al. |
| 5,562,608 A | 10/1996 | Sekins et al. |
| 5,575,803 A | 11/1996 | Cooper et al. |
| 5,584,872 A | 12/1996 | LaFontaine et al. |
| 5,591,157 A | 1/1997 | Hennings et al. |
| 5,591,162 A | 1/1997 | Fletcher et al. |
| 5,616,120 A | 4/1997 | Andrew et al. |
| 5,620,440 A | 4/1997 | Heckele et al. |
| 5,669,907 A | 9/1997 | Platt et al. |
| 5,681,282 A | 10/1997 | Eggers et al. |
| 5,683,366 A | 11/1997 | Eggers et al. |
| 5,695,507 A | 12/1997 | Auth et al. |
| 5,697,281 A | 12/1997 | Eggers et al. |
| 5,697,536 A | 12/1997 | Eggers et al. |
| 5,697,882 A | 12/1997 | Eggers et al. |
| 5,697,909 A | 12/1997 | Eggers et al. |
| 5,700,262 A | 12/1997 | Acosta et al. |
| 5,707,352 A | 1/1998 | Sekins et al. |
| 5,735,811 A | 4/1998 | Brisken |
| 5,741,247 A | 4/1998 | Rizoiu et al. |
| 5,741,248 A | 4/1998 | Stern et al. |
| 5,752,965 A | 5/1998 | Francis et al. |
| 5,755,753 A | 5/1998 | Knowlton |
| 5,782,914 A | 7/1998 | Schankereli |
| 5,785,521 A | 7/1998 | Rizoiu et al. |
| 5,800,482 A | 9/1998 | Pomeranz et al. |
| 5,810,764 A | 9/1998 | Eggers et al. |
| 5,824,703 A | 10/1998 | Clark, Jr. |
| 5,827,268 A | 10/1998 | Laufer |
| 5,843,019 A | 12/1998 | Eggers et al. |
| 5,843,073 A | 12/1998 | Sinofsky |
| 5,871,469 A | 2/1999 | Eggers |
| 5,879,329 A | 3/1999 | Ginsburg |
| 5,885,243 A | 3/1999 | Capetan et al. |
| 5,888,198 A | 3/1999 | Eggers et al. |
| 5,891,095 A | 4/1999 | Eggers et al. |
| 5,891,134 A | 4/1999 | Goble et al. |
| 5,913,856 A | 6/1999 | Chia et al. |
| 5,944,686 A | 8/1999 | Patterson et al. |
| 5,944,715 A | 8/1999 | Goble et al. |
| 5,957,919 A | 9/1999 | Laufer |
| 5,964,752 A | 10/1999 | Stone |
| 5,968,037 A | 10/1999 | Rizoiu |
| 5,980,504 A | 11/1999 | Sharkey et al. |
| 5,986,662 A | 11/1999 | Argiro et al. |
| 5,989,212 A | 11/1999 | Sussman et al. |
| 5,989,238 A | 11/1999 | Ginsburg |
| 5,989,249 A | 11/1999 | Kirwan |
| 5,989,445 A | 11/1999 | Wise et al. |
| 5,997,499 A | 12/1999 | Sussman et al. |
| 6,024,733 A | 2/2000 | Eggers et al. |
| 6,027,501 A | 2/2000 | Goble et al. |
| 6,032,077 A | 2/2000 | Pomeranz |
| 6,032,674 A | 3/2000 | Eggers et al. |
| 6,047,700 A | 4/2000 | Eggers et al. |
| 6,053,909 A | 4/2000 | Shadduck |
| 6,056,746 A | 5/2000 | Goble et al. |
| 6,059,011 A | 5/2000 | Giolo |
| 6,063,079 A | 5/2000 | Hovda et al. |
| 6,063,081 A | 5/2000 | Mulier et al. |
| 6,066,134 A | 5/2000 | Eggers et al. |
| 6,074,358 A | 6/2000 | Andrew et al. |
| 6,080,128 A | 6/2000 | Sussman et al. |
| 6,080,151 A | 6/2000 | Swartz et al. |
| 6,083,255 A | 7/2000 | Laufer et al. |
| 6,095,149 A | 8/2000 | Sharkey et al. |
| 6,099,251 A | 8/2000 | LaFleur |
| 6,102,046 A | 8/2000 | Weinstein et al. |
| 6,102,885 A | 8/2000 | Bass |
| 6,106,516 A | 8/2000 | Bmassengill |
| 6,110,162 A | 8/2000 | Sussman et al. |
| 6,113,722 A | 9/2000 | Hoffman et al. |
| 6,126,682 A | 10/2000 | Sharkey et al. |
| 6,130,671 A | 10/2000 | Argiro |
| 6,139,571 A | 10/2000 | Fuller et al. |
| 6,149,620 A | 11/2000 | Eggers et al. |
| 6,156,036 A | 12/2000 | Sussman et al. |
| 6,159,194 A | 12/2000 | Eggers et al. |
| 6,162,232 A | 12/2000 | Shadduck |
| 6,168,594 B1 | 1/2001 | LaFontaine et al. |
| 6,174,308 B1 | 1/2001 | Goble et al. |
| 6,179,805 B1 | 1/2001 | Sussman et al. |
| 6,190,381 B1 | 2/2001 | Olsen et al. |
| 6,194,066 B1 | 2/2001 | Hoffman |
| 6,196,989 B1 | 3/2001 | Padget et al. |
| 6,200,333 B1 | 3/2001 | Laufer |
| 6,206,848 B1 | 3/2001 | Sussman et al. |
| 6,210,404 B1 | 4/2001 | Shadduck |
| 6,210,405 B1 | 4/2001 | Goble et al. |
| 6,219,059 B1 | 4/2001 | Argiro |
| 6,224,592 B1 | 5/2001 | Eggers et al. |
| 6,231,567 B1 | 5/2001 | Rizoiu et al. |
| 6,235,020 B1 | 5/2001 | Cheng et al. |
| 6,238,391 B1 | 5/2001 | Olsen et al. |
| 6,254,597 B1 | 7/2001 | Rizoiu et al. |
| 6,261,286 B1 | 7/2001 | Goble et al. |
| 6,261,311 B1 | 7/2001 | Sharkey et al. |
| 6,264,650 B1 | 7/2001 | Hovda et al. |
| 6,264,651 B1 | 7/2001 | Underwood et al. |
| 6,264,654 B1 | 7/2001 | Swartz et al. |
| 6,277,112 B1 | 8/2001 | Underwood et al. |
| 6,283,961 B1 | 9/2001 | Underwood et al. |
| 6,283,989 B1 | 9/2001 | Laufer et al. |
| 6,287,274 B1 | 9/2001 | Sussman et al. |
| 6,290,715 B1 | 9/2001 | Sharkey et al. |
| 6,296,636 B1 | 10/2001 | Cheng et al. |
| 6,296,638 B1 | 10/2001 | Davison et al. |
| 6,299,633 B1 | 10/2001 | Laufer |
| 6,300,150 B1 | 10/2001 | Venkatasubramanian |
| 6,312,408 B1 | 11/2001 | Eggers et al. |
| 6,312,474 B1 | 11/2001 | Francis et al. |
| 6,315,755 B1 | 11/2001 | Sussman |
| 6,319,222 B1 | 11/2001 | Andrew et al. |
| 6,327,505 B1 | 12/2001 | Medhkour et al. |
| 6,331,171 B1 | 12/2001 | Cohen |
| 6,355,032 B1 | 3/2002 | Hovda et al. |
| 6,375,635 B1 | 4/2002 | Moutafis et al. |
| 6,379,350 B1 | 4/2002 | Sharkey et al. |
| 6,391,025 B1 | 5/2002 | Weinstein et al. |
| 6,394,949 B1 | 5/2002 | Crowley et al. |
| 6,394,996 B1 | 5/2002 | Lawrence et al. |
| 6,398,759 B1 | 6/2002 | Sussman et al. |

| Patent | Kind | Date | Inventor |
|---|---|---|---|
| 6,398,775 | B1 | 6/2002 | Perkins et al. |
| 6,409,723 | B1 | 6/2002 | Edwards |
| 6,416,508 | B1 | 7/2002 | Eggers et al. |
| 6,458,231 | B1 | 10/2002 | Wapner et al. |
| 6,461,350 | B1 | 10/2002 | Underwood et al. |
| 6,464,694 | B1 | 10/2002 | Massengill |
| 6,464,695 | B2 | 10/2002 | Hovda et al. |
| 6,468,270 | B1 | 10/2002 | Hovda et al. |
| 6,468,274 | B1 | 10/2002 | Alleyne et al. |
| 6,468,313 | B1 | 10/2002 | Claeson et al. |
| 6,482,201 | B1 | 11/2002 | Olsen et al. |
| 6,482,202 | B1 | 11/2002 | Goble et al. |
| 6,488,673 | B1 | 12/2002 | Laufer et al. |
| 6,493,589 | B1 | 12/2002 | Medhkour et al. |
| 6,500,173 | B2 | 12/2002 | Underwood et al. |
| 6,508,816 | B2 | 1/2003 | Shadduck |
| 6,517,568 | B1 | 2/2003 | Sharkey et al. |
| 6,522,930 | B1 | 2/2003 | Schaer et al. |
| 6,527,761 | B1 | 3/2003 | Soltesz et al. et al. |
| 6,527,766 | B1 | 3/2003 | Bair |
| 6,540,741 | B1 | 4/2003 | Underwood et al. |
| 6,544,211 | B1 | 4/2003 | Andrew et al. |
| 6,544,248 | B1 | 4/2003 | Bass |
| 6,547,810 | B1 | 4/2003 | Sharkey et al. |
| 6,558,379 | B1 | 5/2003 | Batchelor et al. |
| 6,575,929 | B2 | 6/2003 | Sussman et al. |
| 6,575,968 | B1 | 6/2003 | Eggers et al. |
| 6,579,270 | B2 | 6/2003 | Sussman et al. |
| 6,582,423 | B1 | 6/2003 | Thapliyal et al. |
| 6,585,639 | B1 | 7/2003 | Kotmel et al. |
| 6,588,613 | B1 | 7/2003 | Pechenik et al. |
| 6,589,201 | B1 | 7/2003 | Sussman et al. |
| 6,589,204 | B1 | 7/2003 | Sussman et al. |
| 6,592,594 | B2 | 7/2003 | Rimbaugh et al. |
| 6,595,990 | B1 | 7/2003 | Weinstein et al. |
| 6,599,311 | B1 | 7/2003 | Biggs et al. |
| 6,602,248 | B1 | 8/2003 | Sharps et al. |
| 6,605,087 | B2 | 8/2003 | Swartz et al. |
| 6,610,043 | B1 | 8/2003 | Ingenito |
| 6,620,130 | B1 | 9/2003 | Ginsburg |
| 6,620,155 | B2 | 9/2003 | Underwood et al. |
| 6,623,444 | B2 | 9/2003 | Babaev |
| 6,632,193 | B1 | 10/2003 | Davison et al. |
| 6,632,220 | B1 | 10/2003 | Eggers et al. |
| 6,634,363 | B1 | 10/2003 | Danek et al. |
| 6,648,847 | B2 | 11/2003 | Sussman et al. |
| 6,652,594 | B2 | 11/2003 | Francis et al. |
| 6,653,525 | B2 | 11/2003 | Ingenito et al. |
| 6,659,106 | B1 | 12/2003 | Hovda et al. |
| 6,669,685 | B1 | 12/2003 | Rizoiu et al. |
| 6,669,694 | B2 | 12/2003 | Shadduck |
| 6,676,628 | B2 | 1/2004 | Sussman et al. |
| 6,676,629 | B2 | 1/2004 | Andrew et al. |
| 6,679,264 | B1 | 1/2004 | Deem et al. |
| 6,679,879 | B2 | 1/2004 | Shadduck |
| 6,682,520 | B2 | 1/2004 | Ingenito |
| 6,692,494 | B1 | 2/2004 | Cooper et al. |
| 6,695,839 | B2 | 2/2004 | Sharkey et al. |
| 6,699,212 | B1 | 3/2004 | Kadziauskas et al. |
| 6,699,244 | B2 | 3/2004 | Carranza et al. |
| 6,712,811 | B2 | 3/2004 | Underwood et al. |
| 6,712,812 | B2 | 3/2004 | Roschak et al. |
| 6,719,738 | B2 | 4/2004 | Mehier |
| 6,719,754 | B2 | 4/2004 | Underwood et al. |
| 6,723,064 | B2 | 4/2004 | Babaev |
| 6,726,684 | B1 | 4/2004 | Woloszko et al. |
| 6,726,708 | B2 | 4/2004 | Lasheras |
| 6,746,447 | B2 | 6/2004 | Davison et al. |
| 6,755,794 | B2 | 6/2004 | Soukup |
| 6,758,846 | B2 | 7/2004 | Goble et al. |
| 6,763,836 | B2 | 7/2004 | Novak et al. |
| 6,764,487 | B2 | 7/2004 | Mulier et al. |
| 6,766,202 | B2 | 7/2004 | Underwood et al. |
| 6,770,070 | B1 | 8/2004 | Balbierz |
| 6,770,071 | B2 | 8/2004 | Woloszko et al. |
| 6,772,012 | B2 | 8/2004 | Ricart et al. |
| 6,776,765 | B2 | 8/2004 | Soukup et al. |
| 6,780,180 | B1 | 8/2004 | Goble et al. |
| 6,805,130 | B2 | 10/2004 | Tasto et al. |
| 6,832,996 | B2 | 12/2004 | Woloszko et al. |
| 6,837,884 | B2 | 1/2005 | Woloszko |
| 6,837,888 | B2 | 1/2005 | Ciarrocca et al. |
| 6,852,108 | B2 | 2/2005 | Barry et al. |
| 6,860,847 | B2 | 3/2005 | Alferness et al. |
| 6,860,868 | B1 | 3/2005 | Sussman et al. |
| 6,875,194 | B2 | 4/2005 | MacKool |
| 6,896,674 | B1 | 5/2005 | Woloszko et al. |
| 6,896,675 | B2 | 5/2005 | Leung et al. |
| 6,901,927 | B2 | 6/2005 | Deem et al. |
| 6,904,909 | B2 | 6/2005 | Andreas et al. |
| 6,907,881 | B2 | 6/2005 | Suki et al. |
| 6,911,028 | B2 | 6/2005 | Shadduck |
| 6,918,903 | B2 | 7/2005 | Bass |
| 6,921,385 | B2 | 7/2005 | Clements et al. |
| 6,929,640 | B1 | 8/2005 | Underwood et al. |
| 6,949,096 | B2 | 9/2005 | Davison et al. |
| 6,955,675 | B2 * | 10/2005 | Jain .................. 606/41 |
| 6,960,182 | B2 | 11/2005 | Moutafis et al. |
| 6,972,014 | B2 | 12/2005 | Eum et al. |
| 6,986,769 | B2 | 1/2006 | Nelson et al. |
| 6,991,631 | B2 | 1/2006 | Woloszko et al. |
| 7,022,088 | B2 | 4/2006 | Keast et al. |
| 7,031,504 | B1 | 4/2006 | Argiro et al. |
| 7,083,612 | B2 | 8/2006 | Littrup et al. |
| 7,128,748 | B2 | 10/2006 | Mooradian et al. |
| 7,136,064 | B2 | 11/2006 | Zuiderveld |
| 7,144,402 | B2 | 12/2006 | Kuester, III |
| 7,144,588 | B2 | 12/2006 | Oray et al. |
| 7,192,400 | B2 | 3/2007 | Campbell et al. |
| 7,233,820 | B2 | 6/2007 | Gilboa |
| 7,235,070 | B2 | 6/2007 | Vanney |
| 7,335,195 | B2 | 2/2008 | Mehier |
| 7,347,859 | B2 | 3/2008 | Garabedian et al. |
| 7,549,987 | B2 | 6/2009 | Shadduck |
| 7,674,259 | B2 | 3/2010 | Shadduck |
| 2001/0020167 | A1 | 9/2001 | Woloszko et al. |
| 2001/0029370 | A1 | 10/2001 | Hovda et al. |
| 2001/0037106 | A1 | 11/2001 | Shadduck |
| 2002/0049438 | A1 | 4/2002 | Sharkey et al. |
| 2002/0077516 | A1 | 6/2002 | Flanigan |
| 2002/0082667 | A1 | 6/2002 | Shadduck |
| 2002/0095152 | A1 | 7/2002 | Ciarrocca et al. |
| 2002/0111386 | A1 | 8/2002 | Sekins et al. |
| 2002/0161326 | A1 | 10/2002 | Sussman et al. |
| 2002/0177846 | A1 * | 11/2002 | Mulier et al. .................. 606/27 |
| 2002/0193789 | A1 | 12/2002 | Underwood et al. |
| 2003/0028189 | A1 | 2/2003 | Woloszko et al. |
| 2003/0040742 | A1 | 2/2003 | Underwood et al. |
| 2003/0097126 | A1 | 5/2003 | Woloszko et al. |
| 2003/0099279 | A1 | 5/2003 | Venkatasubramanian et al. |
| 2003/0109869 | A1 | 6/2003 | Shadduck |
| 2003/0130655 | A1 | 7/2003 | Woloszko et al. |
| 2003/0130738 | A1 | 7/2003 | Hovda et al. |
| 2003/0158545 | A1 | 8/2003 | Hovda et al. |
| 2003/0163178 | A1 | 8/2003 | Davison et al. |
| 2003/0181922 | A1 | 9/2003 | Alferness |
| 2003/0212395 | A1 | 11/2003 | Woloszko et al. |
| 2003/0225364 | A1 | 12/2003 | Kraft et al. |
| 2004/0024398 | A1 | 2/2004 | Hovda et al. |
| 2004/0024399 | A1 | 2/2004 | Sharps et al. |
| 2004/0031494 | A1 | 2/2004 | Danek et al. |
| 2004/0038868 | A1 | 2/2004 | Ingenito |
| 2004/0047855 | A1 | 3/2004 | Ingenito |
| 2004/0049180 | A1 | 3/2004 | Sharps et al. |
| 2004/0054366 | A1 | 3/2004 | Davison et al. |
| 2004/0055606 | A1 | 3/2004 | Hendricksen et al. |
| 2004/0068256 | A1 | 4/2004 | Rizoiu et al. |
| 2004/0068306 | A1 | 4/2004 | Shadduck |
| 2004/0087937 | A1 | 5/2004 | Eggers et al. |
| 2004/0116922 | A1 | 6/2004 | Hovda et al. |
| 2004/0193150 | A1 | 9/2004 | Sharkey et al. |
| 2004/0199226 | A1 | 10/2004 | Shadduck |
| 2004/0230190 | A1 | 11/2004 | Dahla et al. |
| 2004/0254532 | A1 | 12/2004 | Mehier |
| 2005/0004634 | A1 | 1/2005 | Ricart et al. |
| 2005/0010205 | A1 | 1/2005 | Hovda et al. |
| 2005/0119650 | A1 | 6/2005 | Sanders et al. |
| 2005/0166925 | A1 | 8/2005 | Wilson et al. |

| | | |
|---|---|---|
| 2005/0171582 A1 | 8/2005 | Matlock |
| 2005/0187543 A1 | 8/2005 | Underwood et al. |
| 2005/0215991 A1 | 9/2005 | Altman et al. |
| 2005/0222485 A1 | 10/2005 | Shaw et al. |
| 2005/0228423 A1 | 10/2005 | Khashayar et al. |
| 2005/0228424 A1 | 10/2005 | Khashayar et al. |
| 2005/0240171 A1 | 10/2005 | Forrest |
| 2005/0283143 A1 | 12/2005 | Rizoiu |
| 2006/0004400 A1 | 1/2006 | McGurk et al. |
| 2006/0047291 A1 | 3/2006 | Barry |
| 2006/0100619 A1 | 5/2006 | McClurken et al. |
| 2006/0130830 A1 | 6/2006 | Barry |
| 2006/0161233 A1 | 7/2006 | Barry et al. |
| 2006/0200076 A1 | 9/2006 | Gonzalez et al. |
| 2006/0224154 A1 | 10/2006 | Shadduck et al. |
| 2007/0036417 A1 | 2/2007 | Argiro et al. |
| 2007/0091087 A1 | 4/2007 | Zuiderveld |
| 2008/0033493 A1 | 2/2008 | Deckman et al. |
| 2008/0103566 A1 | 5/2008 | Mehier |
| 2008/0110457 A1 | 5/2008 | Barry et al. |
| 2008/0114297 A1 | 5/2008 | Barry et al. |
| 2008/0132826 A1 | 6/2008 | Shadduck et al. |
| 2009/0105702 A1 | 4/2009 | Shadduck |
| 2009/0105703 A1 | 4/2009 | Shadduck |
| 2009/0149846 A1 | 6/2009 | Hoey et al. |
| 2009/0216220 A1 | 8/2009 | Hoey et al. |
| 2009/0312753 A1 | 12/2009 | Shadduck |
| 2010/0076416 A1 | 3/2010 | Hoey et al. |
| 2010/0160905 A1 | 6/2010 | Shadduck |
| 2010/0204688 A1 | 8/2010 | Hoey et al. |

FOREIGN PATENT DOCUMENTS

| | | |
|---|---|---|
| WO | WO 00/29055 | 5/2000 |
| WO | WO 02/069821 | 9/2002 |
| WO | WO 03/070302 | 8/2003 |
| WO | WO 03/086498 | 10/2003 |
| WO | WO 2005/025635 | 3/2005 |
| WO | WO 2005/102175 | 11/2005 |
| WO | WO 2006/003665 | 1/2006 |
| WO | WO 20091009398 | 1/2009 |

OTHER PUBLICATIONS

U.S. Appl. No. 09/762,649, filed Feb. 12, 2001, in the name of Shadduck, Notice of Allowance mailed Sep. 9, 2002.
U.S. Appl. No. 10/017,582, filed Dec. 7, 2001, in the name of Shadduck, Non-Final Rejection mailed Dec. 10, 2002.
U.S. Appl. No. 10/017,582, filed Dec. 7, 2001, in the name of Shadduck, Non-Final Rejection mailed Jul. 17, 2003.
U.S. Appl. No. 10/346,877, filed Jan. 16, 2003, in the name of Shadduck, Examiner's Amendment mailed Mar. 7, 2005.
U.S. Appl. No. 10/346,877, filed Jan. 18, 2003, in the name of Shadduck, Non-Final Rejection mailed Sep. 30, 2004.
U.S. Appl. No. 10/346,877, filed Jan. 18, 2003, in the name of Shadduck, Notice of Allowance mailed Mar. 7, 2005.
U.S. Appl. No. 10/681,625, filed Oct. 7, 2003, in the name of Shadduck, Final Rejection mailed Jun. 3, 2008.
U.S. Appl. No. 10/681,625, filed Oct. 7, 2003, in the name of Shadduck, Non-Final Rejection mailed Aug. 15, 2007.
U.S. Appl. No. 10/681,625, filed Oct. 7, 2003, in the name of Shadduck, Non-Final Rejection mailed Mar. 13, 2009.
U.S. Appl. No. 10/681,625, filed Oct. 7, 2003, in the name of Shadduck, Notice of Allowance mailed Dec. 30, 2009.
U.S. Appl. No. 11/158,930, filed Jun. 22, 2005, in the name of Shadduck, Non-Final Rejection mailed Jun. 24, 2009.
U.S. Appl. No. 12/465,927, filed May 14, 2009, in the name of Shadduck, entitled "Thermotherapy device".
Coda, et al., "Effects of pulmonary reventilation on gas exchange after cryolytic disobstruction of endobronchial tumors," *Minerva Medical*, vol. 72, pp. 1627-1631, Jun. 1981 (with English translation).
Fishman et al., "A randomized trial comparing lung-volume-reduction surgery with medical therapy for severe emphysema," *N Engl J Med*, vol. 348, No. 21, pp. 2059-2073, May 22, 2003.
Homasson. et al., "Bronchoscopic cryotherapy for airway strictures caused by tumors," *Chest*, vol. 90, No. 2, pp. 159-164, Aug. 1986.
International Patent Application No. PCT/US2008/069094 in the name of TSUNAMI MEDTECH, LLC, filed Jul. 2, 2008, International Search Report and Written Opinion mailed Oct. 9, 2008.
Li, K., "Efficient optimal net surface detection for image segmentation— from theory to practice," M.Sc. Thesis, The University of Iowa, 2003.
Marasso, et al., "Cryosurgery in bronchoscopic treatment of tracheobronchial stenosis," *Chest*, vol. 103, No. 2, pp. 472-474, Feb. 1993.
Marasso, et al., "Radiofrequency resection of bronchial tumours in combination, with cryotherapy: evaluation of a new technique," *Thorax*, vol, 53, pp. 106-109, 1998.
Mathur et al., "Fiberoptic bronchoscopic cryotherapy in the management of tracheobronchial obstruction," *Chest*, vol, 110, No. 3, pp. 718-723, Sep. 1996.
Morice et al. "Endobrinchial argon plasma coagulation for treatment of hemotysis and neoptastic airway obstruction," *Chest*, vol, 119, No. 3, pp. 781-787, Mar. 2001.
Quin, J., "Use of neodymium yttrium aluminum garnet laser in long-term palliation of airway obstruction," *Connecticut Medicine*, vol. 59, No. 7, pp. 407-412, Jul. 1995.
Sutedja, et al., "Bronchoscopic treatment of lung tumors," *Elsevier, Lung Cancer*, 11, pp. 1-17, 1994.
Topaz, et al., "Acute Results, Complications, and Effect of Lesion Characteristics on Outcome With the Solid-State, Pulsed Wave, Mid-Infrared Laser Angioplasty System", *Laser in Surg. & Med.*, vol. 22, pp. 228-239, 1998.
Tschirren et al.; "Intrathoracic airway trees: segmentation and airway morphology analysis from low-dose CT scans;" *IEEE Trans. Med. Imaging*, vol, 24, No. 12; pp. 1529-1539. Dec. 2005.
Tschirren, J., "Segmentation, anatomical labeling, branchpoint matching, and quantitative analysis of human airway trees in volumetric CT images," Ph,D. Thesis, The University of Iowa, 231 pages, Aug. 2003.
Tschirren, J., "Segmentation, anatomical labeling, branchpoint matching, and quantitative analysis of human airway trees in volumetric CT images," Slides from Ph.D defense, University of Iowa, 130 pages, Aug. 2003.
U.S. Appl. No. 09/782,649 filed Feb. 12, 2001, in the name of Shadduck, Notice of Allowance mailed Sep. 10, 2002.
U.S. Appl. No. 10/346,877 filed Jan. 18, 2003, in the name of Shadduck, Examiner's Amendment mailed Mar. 2, 2005.
U.S. Appl. No. 10/830,372 filed Apr. 22, 2004, in the name of Shadduck, Examiner Interview Summary mailed Feb. 12, 2008.
U.S. Appl. No. 10/830,372 filed Apr. 22, 2004, in the name of Shadduck, final Office Action mailed May 21, 2008.
U.S. Appl. No. 10/830,372 filed Apr. 22, 2004, in the name of Shadduck, non-final Office Action mailed Aug. 15, 2007.
U.S. Appl. No. 10/830,372 filed Apr. 22, 2004, in the name of Shadduck, Notice of Allowance mailed Apr. 7, 2009.
U.S. Appl. No. 11/158,930 filed Jun. 22, 2005, in the name of Shadduck, non-Office Action mailed Dec. 24. 2009.
U.S. Appl. No. 11/158,930 filed Jun. 22, 2005, in the name of Shadduck, Notice of Allowance mailed Jul. 22, 2010.
U.S. Appl. No. 11/158,930 filed Jun. 22, 2005, in the name of Shadduck, Notice of Allowance mailed Oct. 7, 2010.
U.S. Appl. No. 11/329.381 filed Jan. 10, 2006, in the name of Shadduck, final Office Action mailed Jul. 14, 2010.
U.S. Appl. No.11/329,381 filed Jan. 10. 2006, in the name of Shadduck, non-final Office Action mailed Dec. 9, 2009.
Unger, M. et al. "Monolithic Microfabricated Valves and Pumps by Multilayer Soft Lithography," *Science*, vol. 288, pp. 113-116, Apr. 7, 2000, accessed at http://web.mit.edu/thorsen/www/113.pdf.
Xia, Y. et al. "Soft Lithography," *Annu. Rev. Mater. Sci.*, vol. 28, pp. 153-184, 1998, accessed at http://www.bwfoundry.com/xia.pdf.

* cited by examiner

MEDICAL INSTRUMENT AND METHOD OF USE

CROSS-REFERENCE TO RELATED APPLICATIONS

This application claims benefit of Provisional U.S. Patent Application Ser. No. 60/615,900 filed Oct. 5, 2004 titled Medical Instruments and Techniques for Thermally-Mediated Procedures. This application is also a continuation-in-part of U.S. patent application Ser. No. 10/346,877 filed Jan. 18, 2003 now U.S. Pat. No. 6,911,028 titled Medical Instrument Working End and Method for Endoluminal Treatment. This application is also a continuation-in-part of U.S. patent application Ser. No. 10/681,625 filed Oct. 7, 2003 now U.S. Pat. No. 7,674,259 titled Medical Instruments and Techniques for Thermally-Mediated Therapies. The entire contents of the above U.S. patent applications are incorporated herein by this reference and should be considered a part of this specification.

BACKGROUND OF THE INVENTION

1. Field of the Invention

This invention relates to surgical instruments for applying energy to tissue, and more particularly relates to a system for volumetric removal of tissue by means of high velocity ejection of a vapor media from a first vapor port proximate to soft tissue wherein the vapor-to-liquid phase change of the media applies energy to the tissue. Contemporaneously, the system provides a second port coupled to a suction source that cooperates with the first vapor port to suction tissue debris from the targeted site.

2. Description of the Related Art

Various types of radiofrequency (Rf) and laser surgical instruments have been developed for delivering thermal energy to tissue, for example to ablate tissue, to cause hemostasis, to weld tissue or to cause a thermoplastic remodeling of tissue. While such prior art forms of energy delivery are suitable for some applications, Rf and laser energy typically cannot cause highly "controlled" and "localized" thermal effects that are desirable in microsurgeries or other precision surgeries. In general, the non-linear or non-uniform characteristics of tissue affect both laser and Rf energy distributions in tissue.

What is needed for many surgical procedures is an instrument and technique that can controllably deliver energy to tissue for volumetric tissue removal or tissue cutting without the possibility of desiccation or charring of adjacent tissues, and without collateral thermal damage.

SUMMARY OF THE INVENTION

The present invention is adapted to provide improved methods of controlled energy delivery to localized tissue volumes, for example for volumetric tissue removal or thermoplastic remodeling of tissue.

In general, the thermally-mediated treatment method comprises causing a vapor-to-liquid phase state change in a selected media at a targeted tissue site thereby applying thermal energy substantially equal to the heat of vaporization of the selected media to said tissue site. The thermally-mediated therapy can be delivered to tissue by such vapor-to-liquid phase transitions, or "internal energy" releases, about the working surfaces of several types of instruments for endoluminal treatments or for soft tissue thermotherapies. FIGS. 1A and 1B illustrate the phenomena of phase transitional releases of internal energies. Such internal energy involves energy on the molecular and atomic scale and in polyatomic gases is directly related to intermolecular attractive forces, as well as rotational and vibrational kinetic energy. In other words, the method of the invention exploits the phenomenon of internal energy transitions between gaseous and liquid phases that involve very large amounts of energy compared to specific heat.

It has been found that the controlled application of internal energies in an introduced media-tissue interaction solves many of the vexing problems associated with energy-tissue interactions in Rf, laser and ultrasound modalities. The apparatus of the invention provides a fluid-carrying chamber in the interior of the device or working end. A source provides liquid media to the interior chamber wherein energy is applied to instantly vaporize the media. In the process of the liquid-to-vapor phase transition of a saline media in the interior of the working end, large amounts of energy are added to overcome the cohesive forces between molecules in the liquid, and an additional amount of energy is requires to expand the liquid 1000+ percent (PΔD) into a resulting vapor phase (see FIG. 1A). Conversely, in the vapor-to-liquid transition, such energy will be released at the phase transitions at the targeted tissue interface. That is, the heat of vaporization is released in tissue when the media transitioning from gaseous phase to liquid phase wherein the random, disordered motion of molecules in the vapor regain cohesion to convert to a liquid media. This release of energy (defined as the capacity for doing work) relating to intermolecular attractive forces is transformed into therapeutic heat for a thermotherapy within a targeted body structure. Heat flow and work are both ways of transferring energy.

In FIG. 1A, the simplified visualization of internal energy is useful for understanding phase transition phenomena that involve internal energy transitions between liquid and vapor phases. If heat were added at a constant rate in FIG. 1A (graphically represented as 5 calories/gm blocks) to elevate the temperature of water through its phase change to a vapor phase, the additional energy required to achieve the phase change (latent heat of vaporization) is represented by the large number of 110+ blocks of energy at 100° C. in FIG. 1A. Still referring to FIG. 1A, it can be easily understood that all other prior art ablation modalities—Rf, laser, microwave and ultrasound—create energy densities by simply ramping up calories/gm as indicated by the temperature range from 37° C. through 100° C. as in FIG. 1A. The prior art modalities make no use of the phenomenon of phase transition energies as depicted in FIG. 1A.

FIG. 1B graphically represents a block diagram relating to energy delivery aspects of the present invention. The system provides for insulative containment of an initial primary energy-media within an interior chamber of an instrument's working end. The initial, ascendant energy-media interaction delivers energy sufficient to achieve the heat of vaporization of a selected liquid media such as saline within an interior of the instrument body. This aspect of the technology requires an inventive energy source and controller-since energy application from the source to the selected media (Rf, laser, microwave etc.) must be modulated between very large energy densities to initially surpass the latent heat of vaporization of the media within milliseconds, and possible subsequent lesser energy densities for maintaining the media in its vapor phase. Additionally, the energy delivery system is coupled to a pressure control system for replenishing the selected liquid phase media at the required rate—and optionally for controlling propagation velocity of the vapor phase media from the working end surface of the instrument. In use, the method of the invention comprises the controlled deposition of a large amount of energy—the heat of vaporization as in FIG. 1A—when the vapor-to-liquid phase transition is controlled at the vapor media-tissue interface. The vapor-to-liquid phase transition deposits about 580 cal/gram within the targeted tissue site to perform the thermal ablation.

In one embodiment, the system is configured for ablation and extraction of soft tissue, for example in treating a disc. The flow of vapor is controlled by a computer controller to cause a selected pressure, a selected volume of vapor to be ejected from a working end port. Contemporaneous with tissue contact, the vapor undergoes a vapor-to-liquid phase transition which delivers large amount of energy to the targeted tissue to obliterate or ablate the tissue. In one embodiment, the system causes volumetric removal of tissue by high velocity ejection of the vapor media from a first vapor port. The system provides a second port coupled to a suction source that cooperates with the first vapor port to suction tissue debris from the targeted site.

Additional advantages of the invention will be apparent from the following description, the accompanying drawings and the appended claims.

DETAILED DESCRIPTION OF THE INVENTION

Figure 1A:
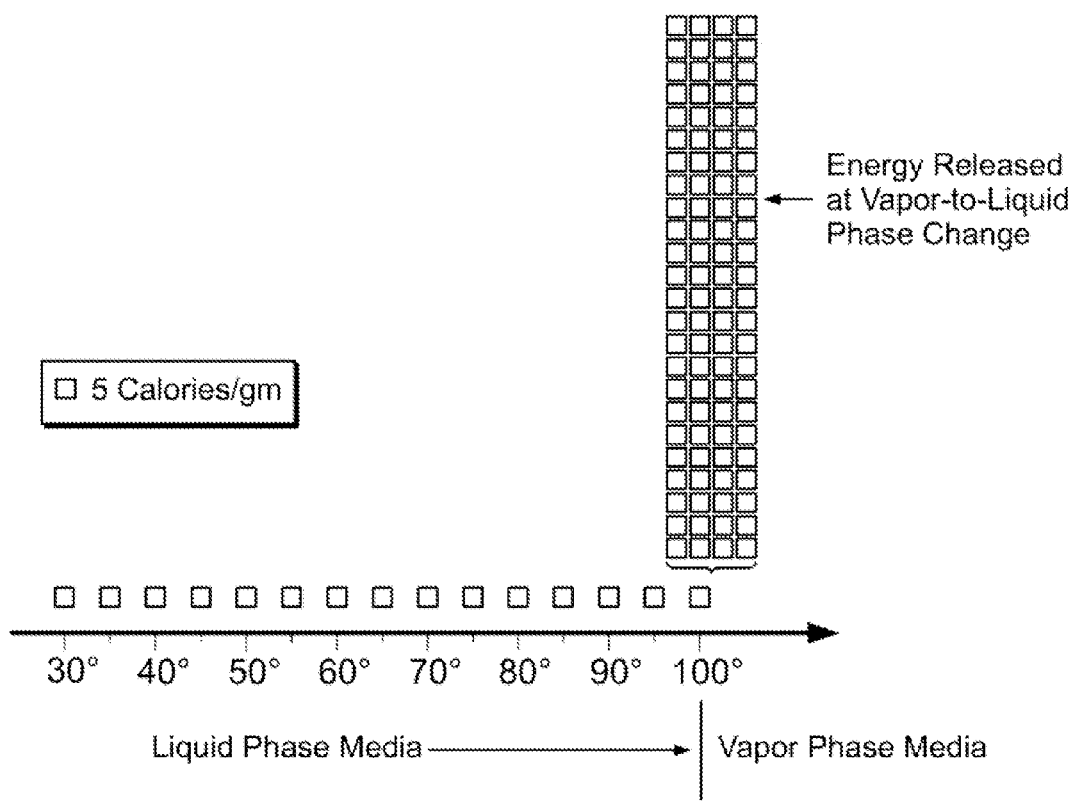
FIG. 1A is a graphical depiction of the quantity of energy needed to achieve the heat of vaporization of water.
Figure 1B:
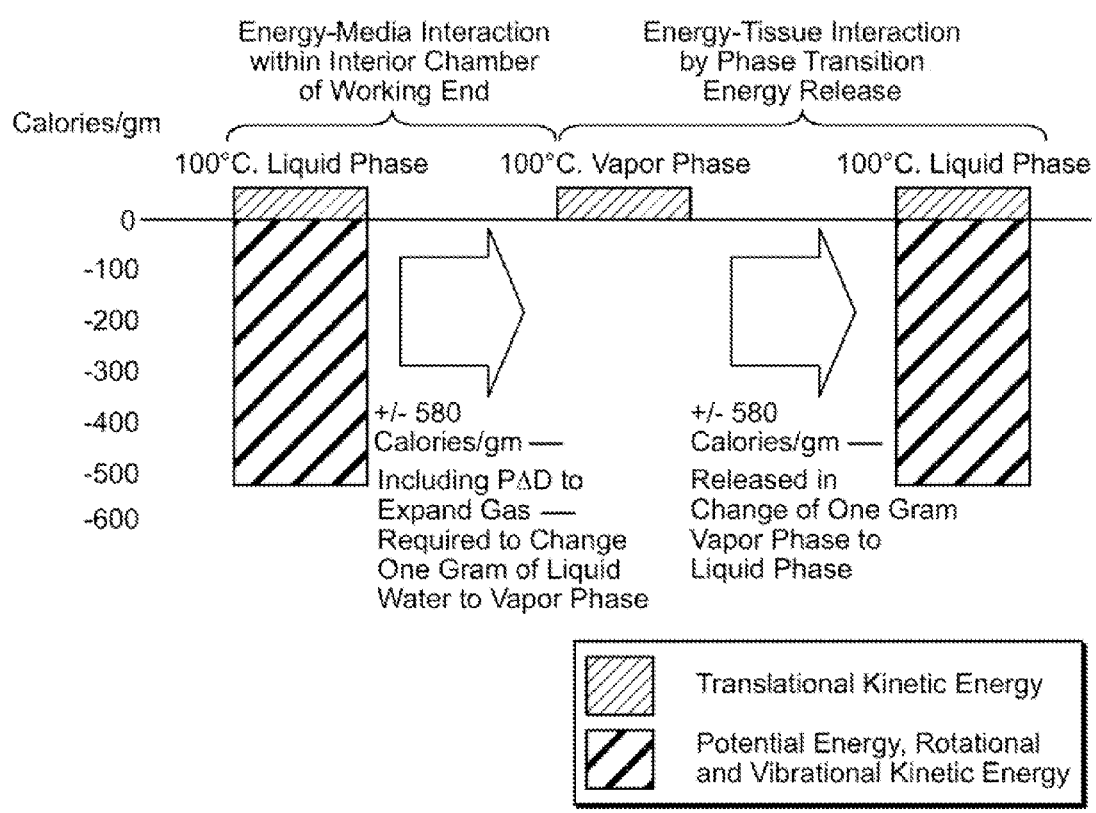
FIG. 1B is a diagram of phase change energy release that underlies one method of the invention.
Figure 2A:
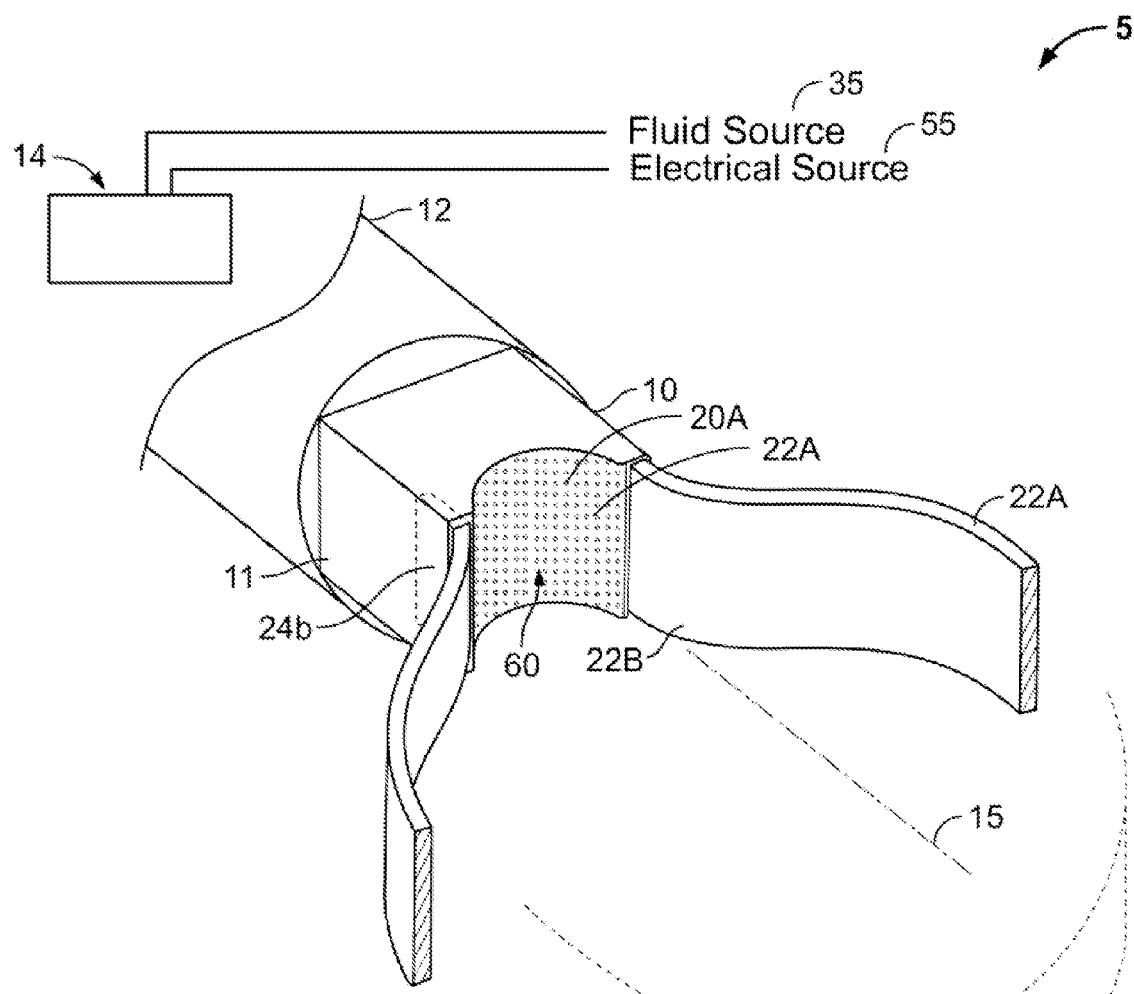
FIG. 2A is a perspective view of the working end of an exemplary Type "A" probe of the present invention with an openable-closeable tissue engaging structure in a first open position.
Figure 2B:
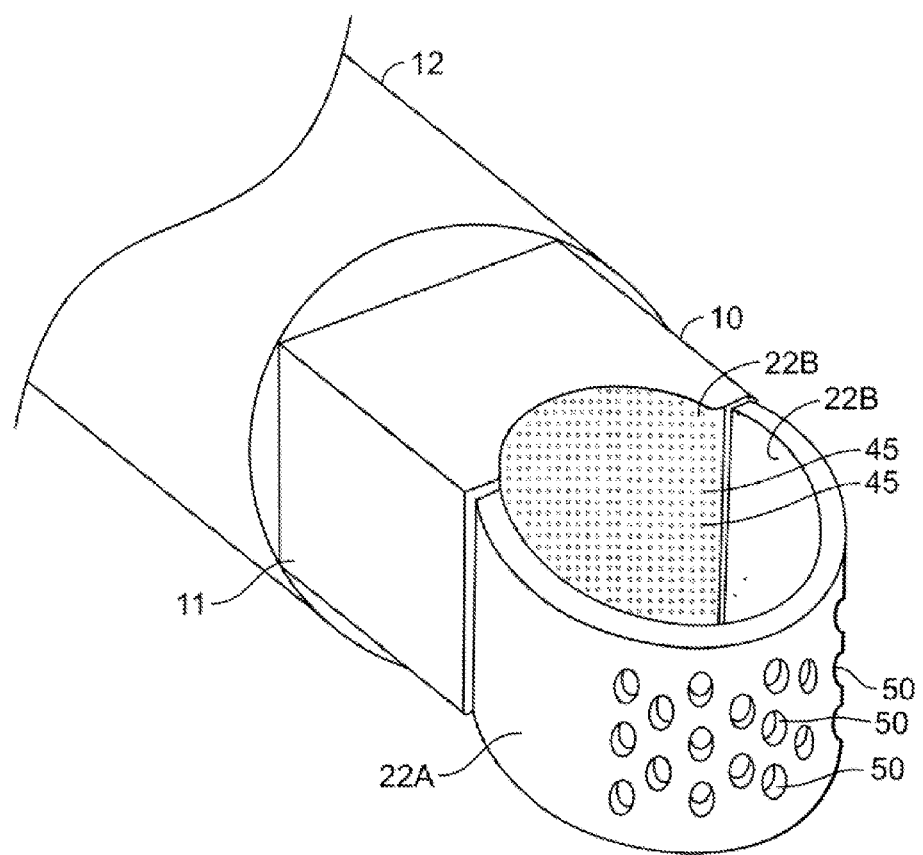
FIG. 2B is a perspective view similar to FIG. 2A probe of the present invention in a second closed position.
Figure 3:
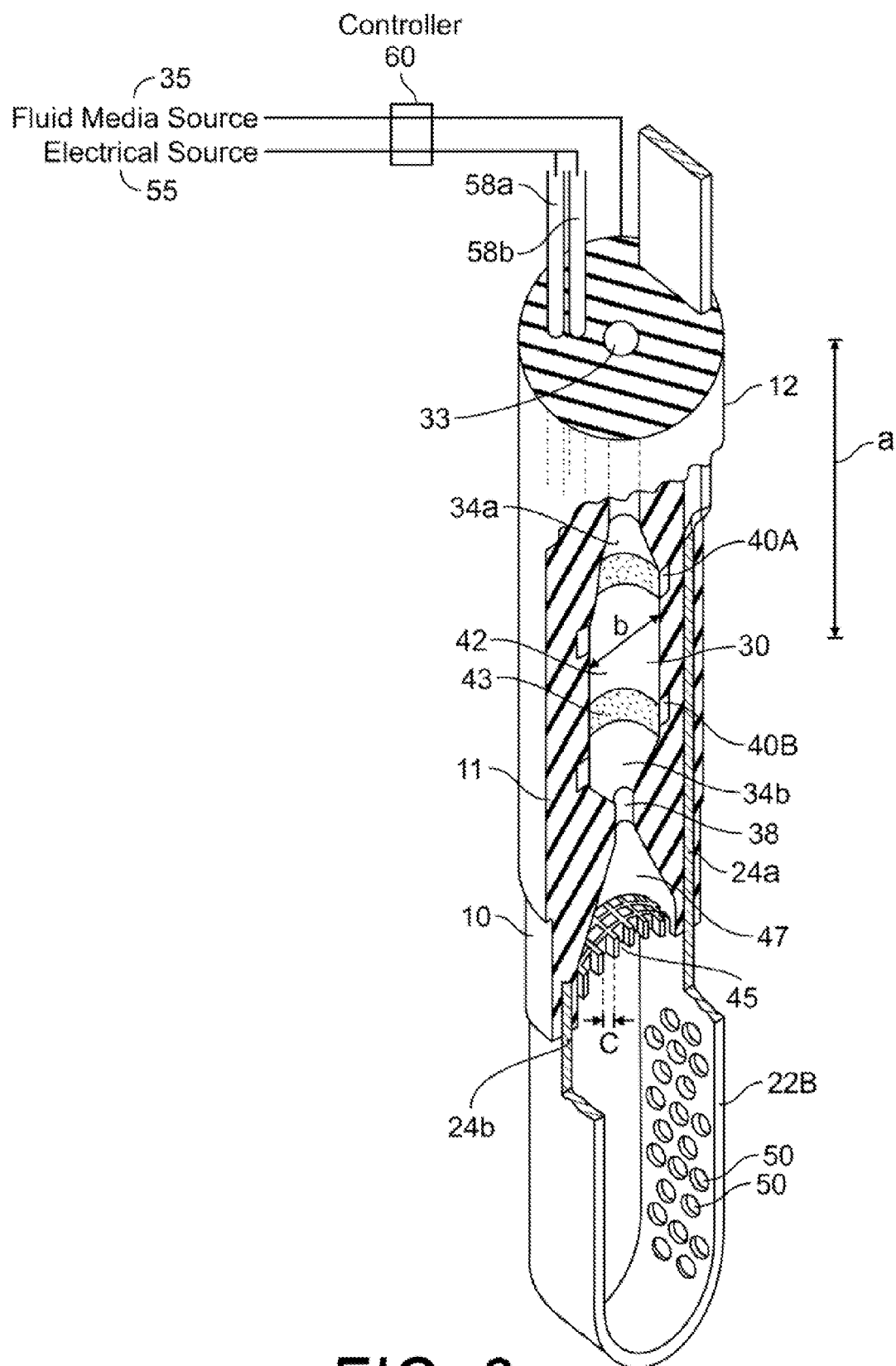
FIG. 3 is a cut-away view of the working end of FIGS. 2A-2B.

1. Type "A" Thermotherapy Instrument. Referring to FIGS. 2A, 2B and 3, the working end 10 of a Type "A" system 5 of the present invention is shown that is adapted for endoscopic procedures in which a tissue volume T targeted for treatment (a thermoplasty) can be captured by a loop structure. The working end 10 comprises a body 11 of insulator material (see FIG. 3) coupled to the distal end of introducer member 12 extending along axis 15. In this exemplary embodiment, the working end 10 has a generally cylindrical cross-section and is made of any suitable material such as plastic, ceramic, glass, metal or a combination thereof. The working end 10 is substantially small in diameter (e.g., 2 mm to 5 mm) and in this embodiment is coupled to an elongate flexible introducer member 12 to cooperate with a working channel in an endoscope. Alternatively, the working end 10 may be coupled to a rigid shaft member having a suitable 1 mm to 5 mm or larger diameter to cooperate with a trocar sleeve for use in endoscopic or microsurgical procedures. A proximal handle portion 14 of the instrument indicated by the block diagram of FIG. 2A carries the various actuator mechanisms known in the art for actuating components of the instrument.

In FIGS. 2A, 2B and 3, it can be seen that the working end 10 carries an openable and closeable structure for capturing tissue between a first tissue-engaging surface 20A and a second tissue-engaging surface 20B. In this exemplary embodiment, the working end 10 and first tissue-engaging surface 20A comprises a non-moving component indicated at 22A that is defined by the exposed distal end of body 11 of working end 10. The second tissue-engaging surface 20B is carried in a moving component that comprises a flexible loop structure indicated at 22B.

The second moving component or flexible loop 22B is actuatable by a slidable portion 24a of the loop that extends through a slot 25 in the working end to an actuator in the handle portion 14 as is known in the art (see FIG. 3). The other end 24b of the loop structure 22B is fixed in body 11. While such an in-line (or axial) flexible slidable member is preferred as the tissue-capturing mechanism for a small diameter flexible catheter-type instrument, it should be appreciated that any openable and closable jaw structure known in the art falls within the scope of the invention, including forms of paired jaws with cam-surface actuation or conventional pin-type hinges and actuator mechanisms. FIG. 2A illustrates the first and second tissue-engaging surfaces 20A and 20B in a first spaced apart or open position. FIG. 2B shows the first and second surfaces 20A and 20B moved toward a second closed position.

Now turning to the fluid-to-gas energy delivery means of the invention, referring to FIG. 3, it can be seen that the insulated or non-conductive body 11 of working end 10 carries an interior chamber indicated at 30 communicating with lumen 33 that are together adapted for delivery and transient confinement of a fluid media M that flows into chamber 30. The chamber 30 communicates via lumen 33 with a fluid media source 35 that may be remote from the device, or a fluid reservoir (coupled to a remote pressure source) carried within introducer 12 or carried within a handle portion 14. The term fluid or flowable media source 35 is defined to include a positive pressure inflow system which preferably is any suitable high pressure pump means known in the art. The fluid delivery lumen 33 transitions to chamber 30 at proximal end portion 34a thereof. The distal end portion 34b of chamber 30 has a reduced cross-section that functions to direct vapor media through a small outlet or nozzle indicated at 38.

Of particular interest, still referring to FIG. 3, paired spaced apart electrode elements 40A and 40B are exposed in surface 42 of interior fluid confinement chamber 30. In this exemplary embodiment, the electrode elements 40A and 40B comprise circumferential exposed surfaces of a conductive material positioned at opposing proximal and distal ends of interior chamber 30, but other arrangements are possible. The invention can utilize any suitable configuration of spaced apart electrodes (e.g., such as concentric electrode surfaces, intertwined helical electrode surfaces, adjustable spaced apart surfaces, or porous electrodes) about at least one confinement chamber 30 or lumen portion of the system. Alternatively, each electrode can comprise one or more projecting elements that project into the chamber. The exemplary embodiment of FIG. 3 shows an elongate chamber having an axial dimension indicated at A and diameter or cross-section indicated at B. The axial dimension may range from about 0.1 mm to 20.0 mm and may be singular or plural as described below. The diameter B may range from micron dimensions (e.g., 0.5 µm) for miniaturized instruments to a larger dimension (e.g., 5.0 mm) for larger instruments for causing the thermally induced liquid-to-vapor transformation required to enable the novel phase change energy-tissue interaction of the invention. The electrodes are of any suitable material such as stainless steel, aluminum, nickel titanium, platinum, gold, or copper. Each electrode surface preferably has a toothed surface texture indicated at 43 that includes hatching, projecting elements or surface asperities for better delivering high energy densities in the fluid proximate to the electrode. The electrical current to the working end 10 may be switched on and off by a foot pedal or any other suitable means such as a switch in handle 14.

FIG. 3 further shows that a preferred shape is formed into the tissue-engaging surface 20A to better perform the method of fusing tissue. As can be seen in FIGS. 2B and 3, the first tissue-engaging surface 20A is generally concave so as to be adapted to receive a greater tissue volume in the central portion of surface 20A. The second tissue-engaging surface 20B is flexible and naturally will be concave in the distal or opposite direction when tissue is engaged between surfaces 20A and 20B. This preferred shape structure allows for controllable compression of the thick targeted tissue volumes T centrally exposed to the energy delivery means and helps prevent conductance of thermal effects to collateral tissue regions CT (see FIG. 4) and as will be described in greater detail below.

FIGS. 2A and 3 show that first tissue-engaging surface 20A defines an open structure of at least one aperture or passageway indicated at 45 that allows vapor to pass therethrough. The apertures 45 may have any cross-sectional shape and linear or angular route through surface 20A with a sectional dimension C in this embodiment ranging upwards from micron dimensions (e.g., 0.5 µm) to about 2.0 mm in a large surface 20A. The exemplary embodiment of FIG. 3 has an expanding cross-section transition chamber 47 proximate to the aperture grid that transitions between the distal end 34b of chamber 30 and the apertures 45. However, it should be appreciated that such a transition chamber 47 is optional and the terminal portion of chamber 30 may directly exit into a plurality of passageways that each communicate with an aperture 45 in the grid of the first engaging surface 20A. In a preferred embodiment, the second tissue-engaging surface 20B defines (optionally) a grid of apertures indicated at 50 that pass through the loop 22B. These apertures 50 may be any suitable dimension (cf. apertures 45) and are adapted to generally oppose the first tissue-engaging surface 20A when the surfaces 20A and 20B are in the second closed position, as shown in FIG. 2B.

The electrodes 40A and 40B of working end 10 have opposing polarities and are coupled to Rf generator or electrical source 55. FIG. 3 shows current-carrying wire leads 58a and 58b that are coupled to electrodes 40A and 40B and extend to electrical source 55 and controller 60. In a preferred embodiment of the invention, either tissue-engaging surface optionally includes a sensor 62 (or sensor array) that is in contact with the targeted tissue surface (see FIG. 2A). Such a sensor, for example a thermocouple known in the art, can measure temperature at the surface of the captured tissue. The sensor is coupled to controller 60 by a lead (not shown) and can be used to modulate or terminate power delivery as will be described next in the method of the invention.

Figure 4:
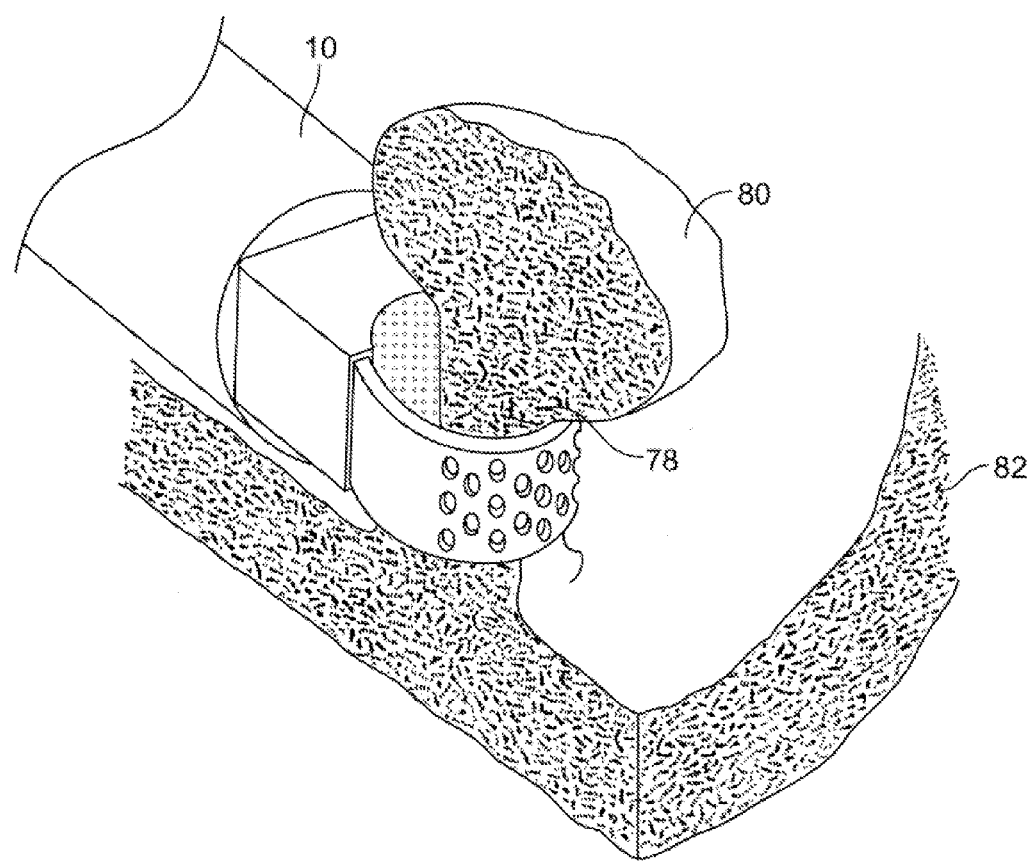
FIG. 4 is a perspective view of the working end of FIG. 3 capturing an exemplary tissue volume.

Operation and use of the working end of FIGS. 2A, 2B and 3 in performing a method of treating tissue can be briefly described as follows, for example in an endoscopic polyp removal procedure. As can be understood from FIG. 4, the working end 10 is carried by an elongate catheter-type member 12 that is introduced through a working channel 70 of an endoscope 72 to a working space. In this case, the tissue T targeted for sealing is a medial portion 78 of a polyp 80 in a colon 82. It can be easily understood that the slidable movement of the loop member 22B can capture the polyp 80 in the device as shown in FIG. 4 after being lassoed. The objective of the tissue treatment is to seal the medial portion of the polyp with the inventive thermotherapy. Thereafter, utilize a separate cutting instrument is used to cut through the sealed portion, and the excised polyp is retrieved for biopsy purposes.

Figure 5:
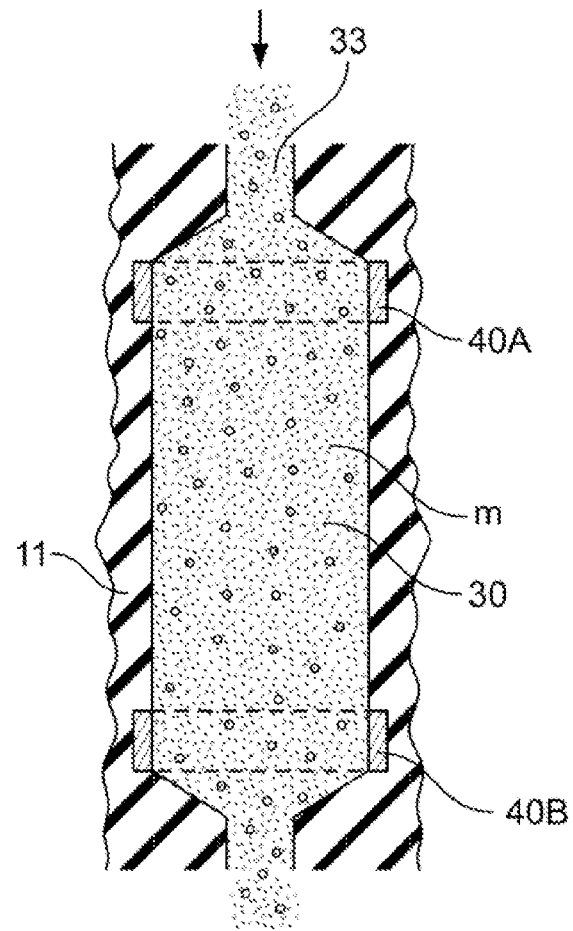
FIGS. 5-6 are sectional schematic views of working end of FIG. 3 depicting, in sequence, the steps of a method of the present invention to seal or weld a targeted tissue volume, FIG. 5 illustrating the pressurized delivery of a liquid media to an interior channel, and FIG. 6 depicting an electrical discharge that causes a liquid-to-gas phase change as well as the ejection of the vapor media into the targeted tissue to thermally seal engaged tissue.
Figure 5:
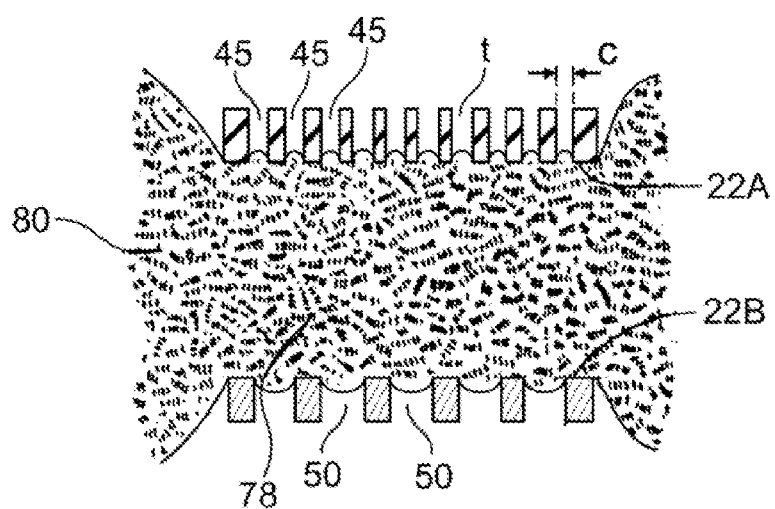
Figure 6:
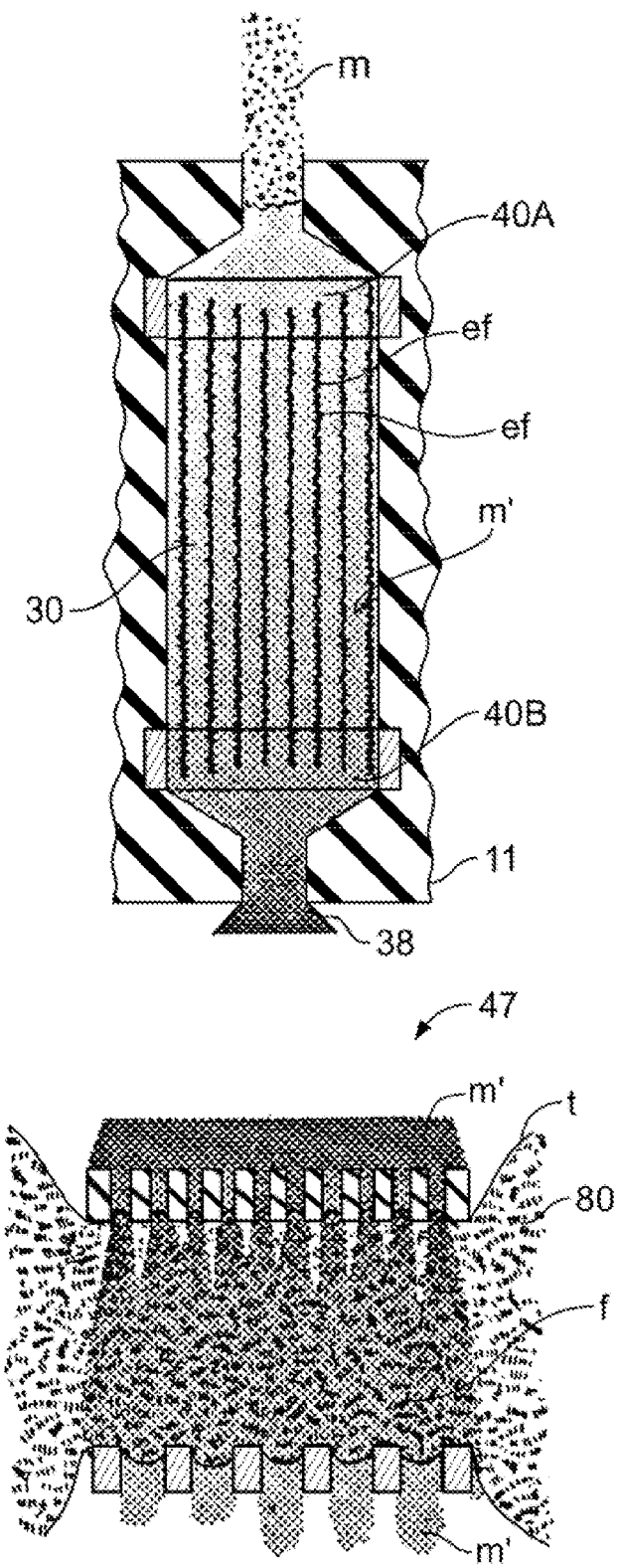

Now turning to FIGS. 5 and 6, two sequential schematic views of the working end engaging tissue T are provided to illustrate the energy-tissue interaction caused by the method of the invention. FIG. 5 depicts an initial step of the method wherein the operator sends a signal to the controller 60 to delivery fluid media M (e.g., saline solution or sterile water) through lumen 33 into chamber 30. FIG. 6 depicts the next step of the method wherein the controller delivers an intense discharge of electrical energy to the paired electrode elements 40A and 40B within chamber 30 indicated by electric arc or electric field EF. The electrical discharge provides energy exceeding the heat of vaporization of the contained fluid volume. The explosive vaporization of fluid media M (of FIG. 5) into a vapor or gas media is indicated at M' in FIG. 6. The greatly increased volume of gas media M' results in the gas being ejected from chamber 30 at high velocity through apertures 45 of surface 20A into the targeted tissue T. The liquid-to-vapor transition caused by the electrical discharge results in the vapor media M' having a temperature of 100° C. or more as well as carrying the heat of vaporization to deliver thermal effects into or through the targeted tissue T, as indicated graphically by the shaded regions of gas flow in FIG. 6. The fluid source and its pressure mechanism can provide any desired level of vapor ejection pressure. Depending on the character of the introduced liquid media, the media is altered from a first lesser temperature to a second greater temperature in the range of 100° C. or higher depending on pressure. The ejection of vapor media M' and its condensation will uniformly and very rapidly elevate the temperature of the engaged tissue to the desired range of about 65° C. to 100° C. to cause hydrothermal denaturation of proteins in the tissue, and to cause optimal fluid inter-mixing of tissue constituents that will result in an effective seal. In effect, the vapor-to-liquid phase transition of the ejected media M' will deposit heat equal to the heat of vaporization (also sometimes called the heat of condensation) in the tissue. At the same time, as the heat of vaporization of media M' is absorbed by water in the targeted tissue, the media converts back to a liquid thus hydrating the targeted tissue T. Such protein denaturation by hydrothermal effects differentiates this method of tissue sealing or fusion from all other forms of energy delivery, such as radiofrequency energy delivery. All other forms of energy delivery vaporize intra- and extracellular fluids and cause tissue desiccation, dehydration or charring which is undesirable for the intermixing of denatured tissue constituents into a proteinaceous amalgam.

The above electrical energy deliver step is continuous or can be repeated at a high repetition rate to cause a pulsed form of thermal energy delivery in the engaged tissue. The fluid media M inflow may be continuous or pulsed to substantially fill chamber 30 before an electrical discharge is caused therein. The repetition rate of electrical discharges may be from about 1 Hz to 1000 Hz. More preferably, the repetition rate is from about 10 Hz to 200 Hz. The selected repetition rate preferably provides an interval between electrical discharges that allows for thermal relaxation of tissue, that may range from about 10 ms to 500 ms. The electrical source or voltage source 55 may provide a voltage ranging between about 20 volts and 10,000 volts to cause instant vaporization of the volume of fluid media M captured between the electrode elements 40A and 40B. After a selected time interval of such energy application to tissue T, that may range from about 1 second to 30 seconds, and preferably from about 5 to 20 seconds, the engaged tissue will be contain a core region in which the tissue constituents are denatured and intermixed under relatively high compression between surfaces 20A and 20B. Upon disengagement and cooling of the targeted tissue T, the treated tissue will be fused or welded. Over time, the body's wound healing response will reconstitute the treated tissue by means of fibrosis to create a collagenous volume or scar-like tissue.

Figure 7:
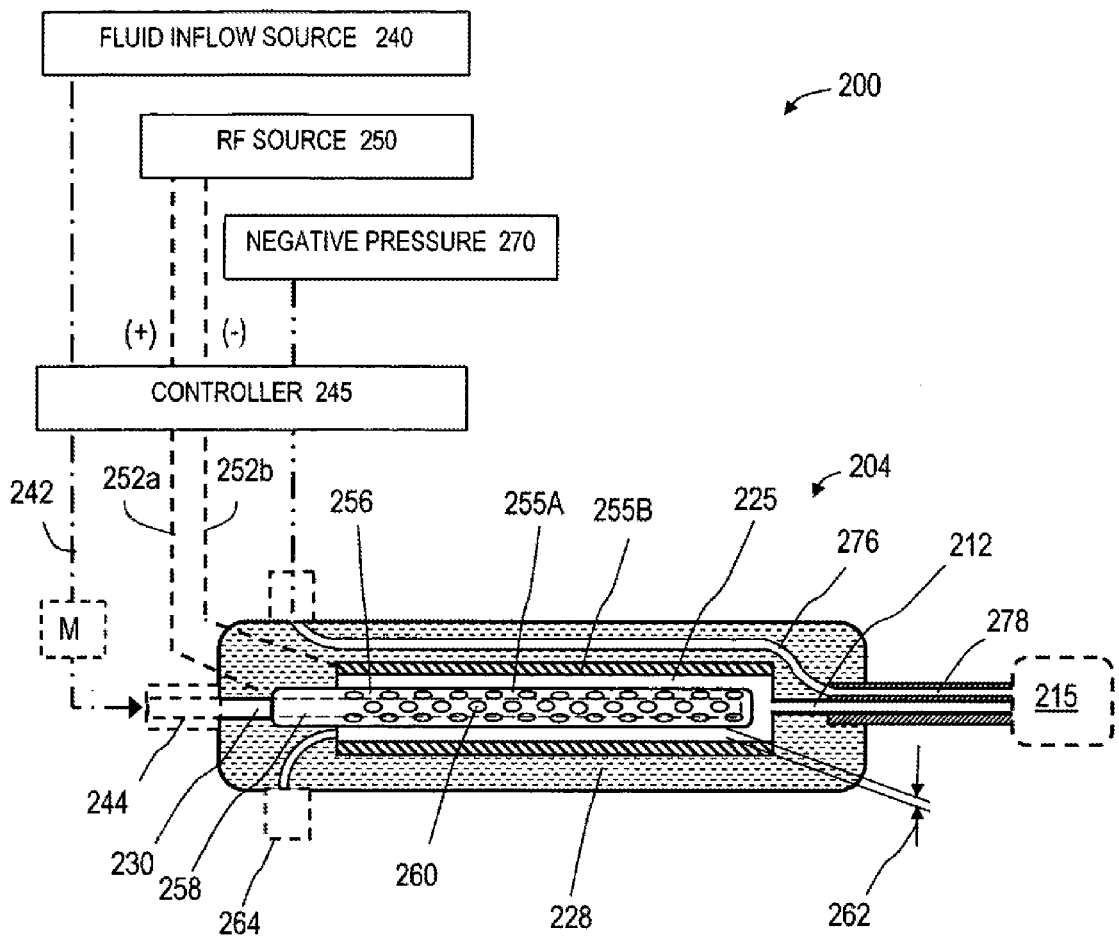
FIG. 7 a cut-away of a Type "B" system with a thermal energy delivery mechanism for a liquid-to-vapor conversion of a pressurized inflow of a saline solution in a probe handle that is coupled to an elongated introducer with a working end configured for delivery of vapor to soft tissue, such as a disc nucleus.
Figure 8:
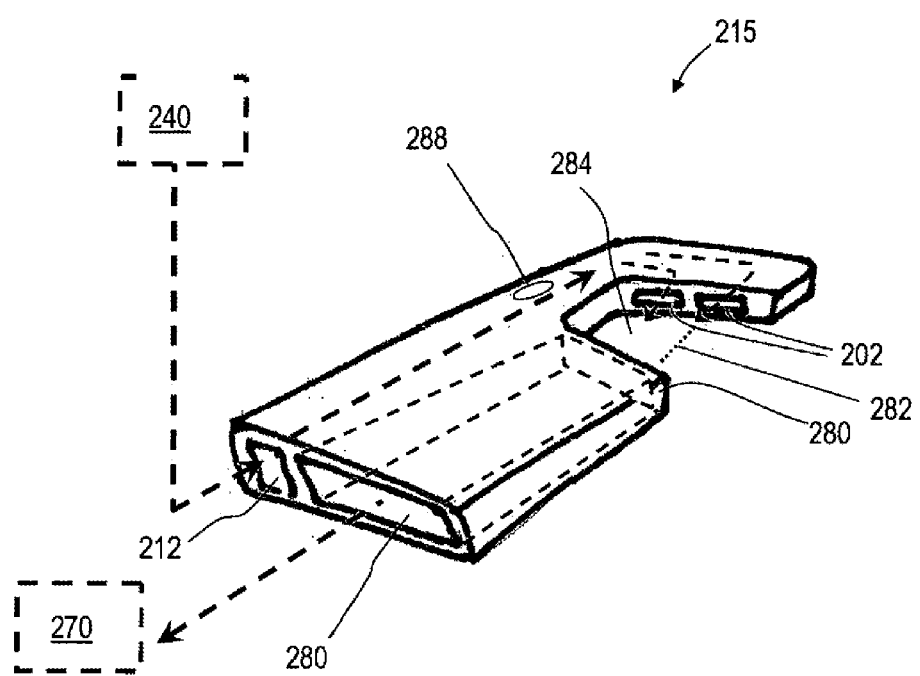
FIG. 8 is view of a working end of the probe of FIG. 7.

2. Type "B" Thermotherapy Instrument. Now referring to FIGS. 7 and 8, another embodiment of vapor generation and delivery system 200 is shown. In the previous embodiment, the working end was optimized for engaging and sealing tissue with a working surface that is in contact with tissue. In the embodiment of FIGS. 7 and 8, the working end ejects vapor from port 202 for the controlled application of energy by means of a vapor-to liquid phase change energy release for soft tissue removal, for example, to remove disc nucleus tissue. The system can also be used for removal of other soft tissue such as adipose tissue, tumors and the like. In one embodiment, the vapor quality is adapted for collapse (condensation) as well the high velocity vapor (and vapor droplets) applying mechanical force to the soft tissue to assist in the tissue obliteration. The system and introducer sleeve 205 as shown in FIGS. 7 and 8 also includes a negative pressure source coupled to an outflow lumen or channel for extracting condensed vapor and tissue debris from the targeted site, as will be described in more detail below.

In FIG. 7, it can be seen that system 200 includes a handle portion 204 that transitions into an introducer sleeve 205 that has an elongated dimension for introduction into a patient's body percutaneously, or through a body cavity or a body lumen. The diameter of introducer sleeve 205 can range from about 1 mm to 6 mm or more. In one embodiment, the introducer sleeve is configured for introduction percutaneously into patient's disc as indicated in FIG. 9.

In one embodiment, the introducer sleeve 205 is fabricated of a temperature resistant polymer or a metal in combination with a polymeric coating. The introducer sleeve 205 can be rigid, deformable or articulatable as in known in the art. In one embodiment, the introducer sleeve 205 is a metal coated with a polymer having a low thermal conductivity, for example less than about 1.0 W/m-K, and preferably less than about 0.50 W/m-K. In one example, an unreinforced polyetheretherketone (PEEK) has a thermal conductivity of about 0.25 W/m-K and can be used for inner and/or outer layers of the introducer. Alternatively, the introducer sleeve 205 can be of PEEK. PEEK is high temperature resistant engineered thermoplastic with excellent chemical and fatigue resistance plus thermal stability. PEEK had a maximum continuous working temperature of 480° F. and retains its mechanical properties up to 570° F. in high-pressure environments. Other materials used in the introducer can comprise formulations or blends of polymers that include, but are not limited to PTFE, polyethylene terephthalate (PET), or PEBAX. PTFE (polytetrafluoroethylene) is a fluoropolymer which has high thermal stability (up to 260° C.), is chemically inert, has a very low dielectric constant, a very low surface friction and is inherently flame retardant. A range of homo and co-fluoropolymers are commercialized under such names as Teflon®, Tefzel®, Neoflon®, Polyflon® and Hyflon®. In another embodiment, the introducer sleeve can carry another layer of a suitable thickness that comprises a low thermal conductivity region such as an air gaps, a layer of an insulative ceramic or glass microspheres or fibers, or at least one lumen that carries a cryofluid in communication with a cryogenic fluid source as in known in the art.

Now turning to FIG. 7, the cut-away view of handle 204 shows that an interior chamber 225 is formed within the interior of an insulator material indicated at 228 such as a ceramic or a combination of materials to insulate the interior chamber 225 from the surface of the handle. An inflow channel 230 communicates with pressurized inflow source 240 of fluid or liquid media via flexible tube 242 coupled to fitting 244. A computer controller 245 is provided to control parameters of fluid inflows to the interior chamber 225. The interior chamber 225 has a distal region in which media flows transition to outflow channel 212 that extends to the working end 215. In FIG. 8, it can be seen that Rf source 250 (also operatively connected to controller 245) has first polarity (+) lead 252a and opposing second polarity (−) lead 252b that are coupled respectively to first and second conductive surfaces or electrodes 255A and 255B exposed in interior chamber 225 that serve as a thermal energy delivery mechanism. The first conductive surface 255A is the outer surface of elongated sleeve 256 with bore 258 therein having diffuser ports 260 in the sleeve wall for introducing pressurized liquid media M into the interior chamber 225. The diffuser ports 260 have a suitable dimension and configuration for diffusing or atomizing a high pressure inflow of flow media M from source 240, which preferably is a saline solution. The second polarity (−) lead is coupled to conductive surface 255B which comprises a radially outward surface of interior chamber 225. In the embodiment shown in FIG. 7, it can be seen that the first and second conductive surfaces 255A and 255B are concentric, extend over a substantial length of the handle and have a large surface area with a fixed spaced apart radial dimension indicated at 262. The radial dimension 262 between the electrode surfaces is selected to match the particular impedance and other operating characteristics of the Rf generator.

The system also includes a negative pressure source 270 that communicates with an outflow channel 276 and outflow lumen 278 in the introducer sleeve, as can be seen in the cut-away view of FIG. 7. In FIG. 8, it can be seen that the working end 215 has a suction port 280 that is configured for the aspiration of tissue debris from the targeted site. The ablation, obliteration and volumetric removal of soft tissue is enabled by the phase change energy release of the vapor transitioning to a liquid as well as mechanical effect of vapor engaging the soft tissue. In the embodiment of FIG. 8, the vapor outlet (or a plurality of outlets) 202 (i) eject vapor along an axis 282 in a recess 284 that is at least in partly oriented toward an axis of the aspiration port 280, or (ii) that deflect vapor toward at least one aspiration port 280. In any embodiment, the inflow pressure of the media can range upward from about 5 psi. In this embodiment, the inflow pressure is elevate greatly to the range of about 5,000 psi to 50,000 psi with a very small media outlet in the range of 0.005" to 0.025" or other suitable dimension and pressure wherein water droplets can apply mechanical energy to scour, damage or obliterate soft tissue. In this embodiment, the system includes the Rf source 250 described above that are operatively coupled to the media inflow pressure source 240 and controller 245 that can apply energy to cause a selected level of vaporization. Optionally, the system can be configured to pulse the energy delivery or the vapor flows at 10 Hz to 500 Hz which it has been found is useful for soft tissue removal. In one method of use, the system can control pressure and flow volume for allowing the vapor flow to obliterate or scour soft disc nucleus tissue while not allowing obliteration of the disc annulus. The system thus allows for tissue-discrimination and ablation based on tissue characteristics such as tissue density, tissue fibrous level and the like. The working end 215 of FIG. 8 is thus well suited for volumetric removal of disc nucleus tissue. Such treatments are needed for new procedures that implant an artificial nucleus, for annulus repair treatments.

Referring to FIG. 7, in a method of operation, the system injects a volume of liquid saline flow media M at a selected rate under pressure from source 240 which is diffused and atomized by ports 260 as the media enters interior chamber 225. Contemporaneous with injection and diffusion of the volume of saline, the system delivers sufficient current from source 250 and controller 245 to the conductive atomized saline via the opposing polarity surfaces 255A and 250B which instantly vaporize the $H_2O$ in the flow media M to generate a vapor M' that is injected from interior chamber 225 into lumen or channel 212 of introducer sleeve 205. The instantaneous increase in volume of media in the liquid-to-vapor phase transition greatly increases interior pressures in interior chamber 225 to thereby accelerate the flow into and through the introducer sleeve to working end 215. Contemporaneous with the ejection of vapor from the working end, the negative pressure source 270 is actuated to suction the collapsing vapor and tissue debris into port 280 and aspiration channel 278. In any embodiment, the vapor aspiration port or ports 280 are substantially larger in cross-section than the vapor outlet or outlets 202 to accommodate the increase in volume of the condensate as well as tissue debris.

Turning back to FIG. 7, the system and handle 204 can include an optional pressure relief valve schematically indicated at 264 so that any overpressures in the interior chamber are released. The release of any overpressure can be vented through an additional lumen in the supply tube 242 or to another chamber in the handle.

Figure 9A:
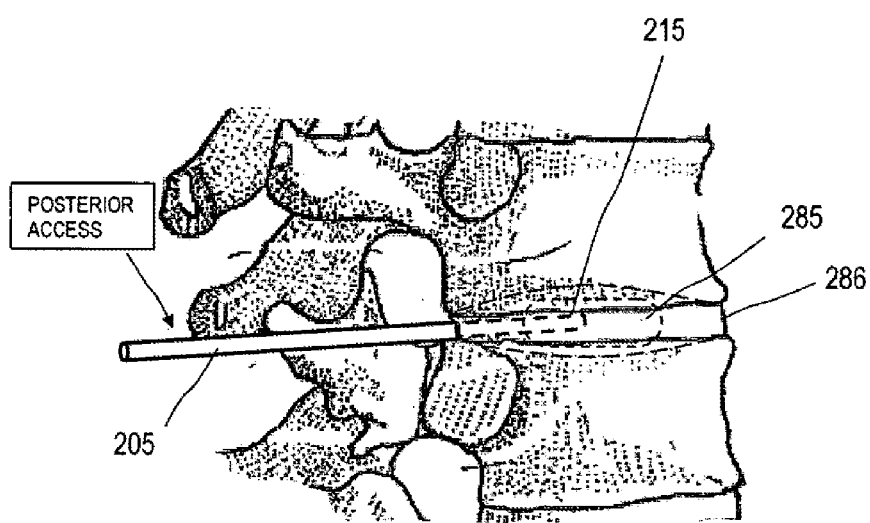
FIG. 9A is a view of a method of using the probe working end of FIG. 8 to volumetrically remove disc nucleus tissue.

FIG. 9A further depicts a method of the invention in treating a patient's disc for removal of a disc nucleus. In FIG. 9A, it can be seen that the physician has navigated the working end 215 to the targeted nucleus region 285 of a disc 286 as in known in the art under imaging such as fluoroscopy. In one embodiment, the working end carries radiopaque marking to allow the physician to see the angular orientation of the working end. In a next step, the physician sets the pressure, volume of vapor and rate of vapor delivery in the fluid inflow controller 245 that is operatively coupled to the fluid source 240, Rf source 250 and negative pressure source 270. The controller 245 operates from pre-sets that select a power level and duration of Rf energy delivery to cooperate with the selected volume of inflowing media M. The controller 245 also operates using pre-sets for simultaneous actuation of the negative pressure source 270 that communicates with lumen 278 in introducer sleeve 205 for suction of tissue debris and vapor condensate. The physician then can move the working end 215 axially, rotationally and angularly to remove the disc nucleus while the preventing damage to the annulus.

Figure 9B:
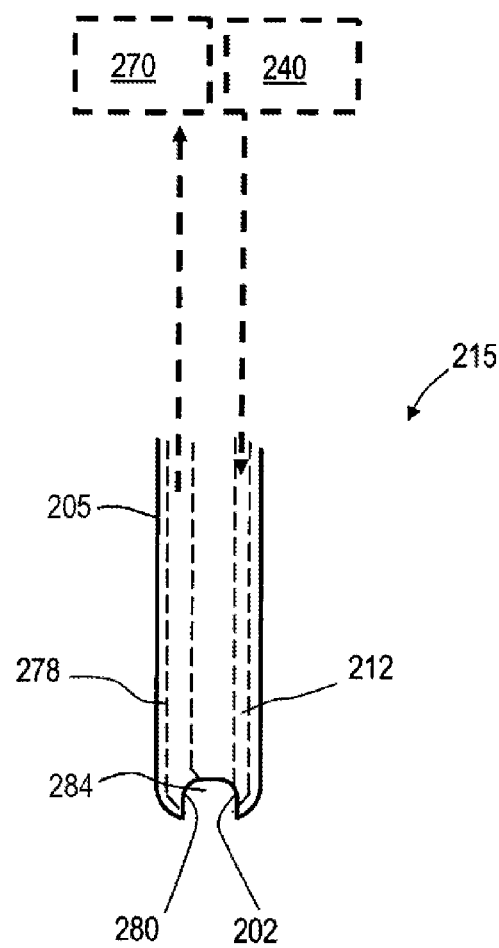
FIG. 9B is a view of an alternative working end similar to FIG. 8.
Figure 9C:
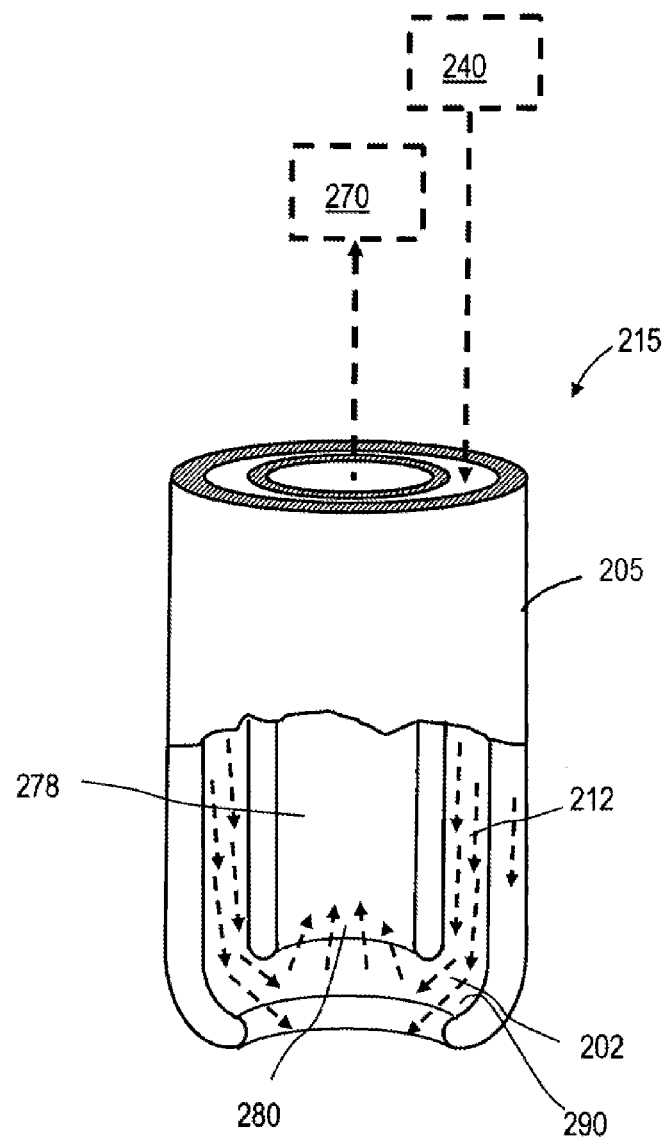
FIG. 9C is a view of another alternative working end similar to FIGS. 8 and 9B.
Figure 9D:
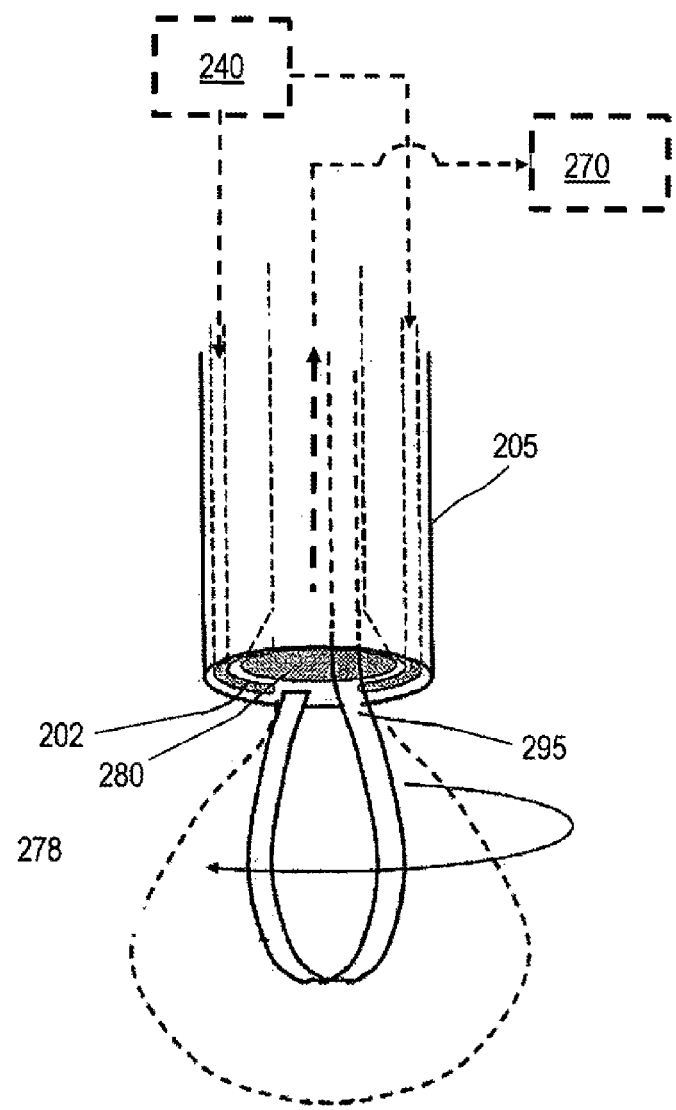
FIG. 9D is a view of another alternative working end similar to that of FIG. 9C with a cutting loop for cutting soft tissue.

FIGS. 9B and 9C illustrate working ends 215 that are similar to that of FIG. 8 with different arrangements of vapor outlets 220 and aspiration ports 280. In FIG. 9B, a recess 284 is at the distal end the introducer sleeve 205 with the vapor outlet 220 and aspiration port 280 generally opposing on another in the recess. In FIG. 9C, the introducer 205 includes a deflector portion indicated at 290 proximate the vapor outlet 202 for deflecting the flow of vapor toward the aspiration port. In the embodiment of FIG. 9C, the vapor inflow channel 212 and the aspiration channel 278 are in a concentric configuration. FIG. 9D illustrates a working end wherein the introducer sleeve 205 is rotatable at high speed together with a loop element 295 that can be deployed from the working end to cut or scour tissue contemporaneous with energy delivery as described above. The loop element can rotate at any speed from about 20 rpm to 10,000 rpm. In one embodiment, the loop 295 is made of a flexible, round cross-section polymer filament. In use, the filament will operate to cut soft tissue but flex to discriminate against cutting harder tissue. This system is useful in discriminating, for example, between the disc nucleus and the annulus. In another embodiment, the loop 295 is a metal with option blade edge that can be used, for example, to excise and extract soft tumor tissue in a breast, liver, lung or the like. The energy delivered by the vapor contemporaneously obliterates the tissue and can thermally seal the cavity created by the tissue extraction.

An optional pressure sensor 288 located at the distal end of the introducer 205 (FIG. 8) can be used to assist in determining pressures in the interior of the patient in a working region. MEMS-fabricated pressure sensors are known in the art and can be carried in the surface of the introducer or the balloon surface, for example, of the type fabricated by Integrated Sensing Systems, Inc., 391 Airport Industrial Drive, Ypsilanti, Mich. 48198. Such sensor can be linked back to controller 245 to adjust aspiration pressures or to terminate vapor flow. The MEMS sensor also can be an accelerometer linked to the controller for modulating or terminating vapor delivery in response to unwanted movement of the working end caused by the high pressure ejection of vapor.

Figure 10:
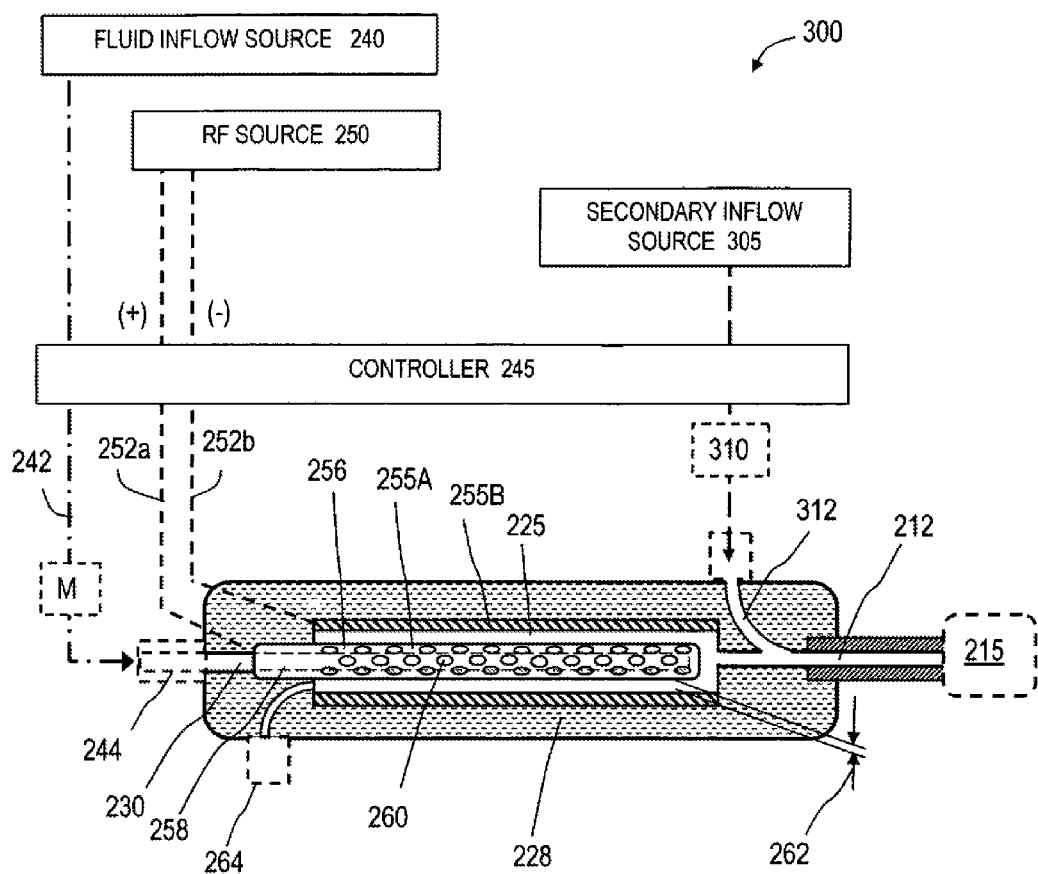
FIG. 10 is another embodiment similar to that of FIG. 7 with an alternative system for delivering vapor to soft tissue together with introducing a second media to control the mass average temperature of the vapor.

In another embodiment and method of the invention, referring to FIG. 10, the system 300 can include a secondary pressurized media inflow source 305 that is adapted to introduce media or substance 310 (in the form of at least one of a gas, liquid or particulate) through channel 312 in the handle into channel 212 to combine with vapor media M' after it is ejected from chamber 225. In a method of the invention, the system thus allows for controlling the average mass temperature of the vapor. In one embodiment, the additional media 310 comprises a bioinert gas or atomized fluid that is depressurized and introduced into the vapor for the purpose of reducing the mass average temperature of the injected media to lower than about 100° C. For example, the introduced media 310 can be depressurized $CO_2$, $N_2$, or $O_2$ or atomized $H_2O$. By this means, the mass average temperature can be less than 100° C., for example in the range of about 45° C. to 100° C. More preferably, the mass average temperature can be in the range of about 60° C. to 95° C. Still more preferably, the mass average temperature can be in the range of about 70° C. to 90° C.

Figure 11:
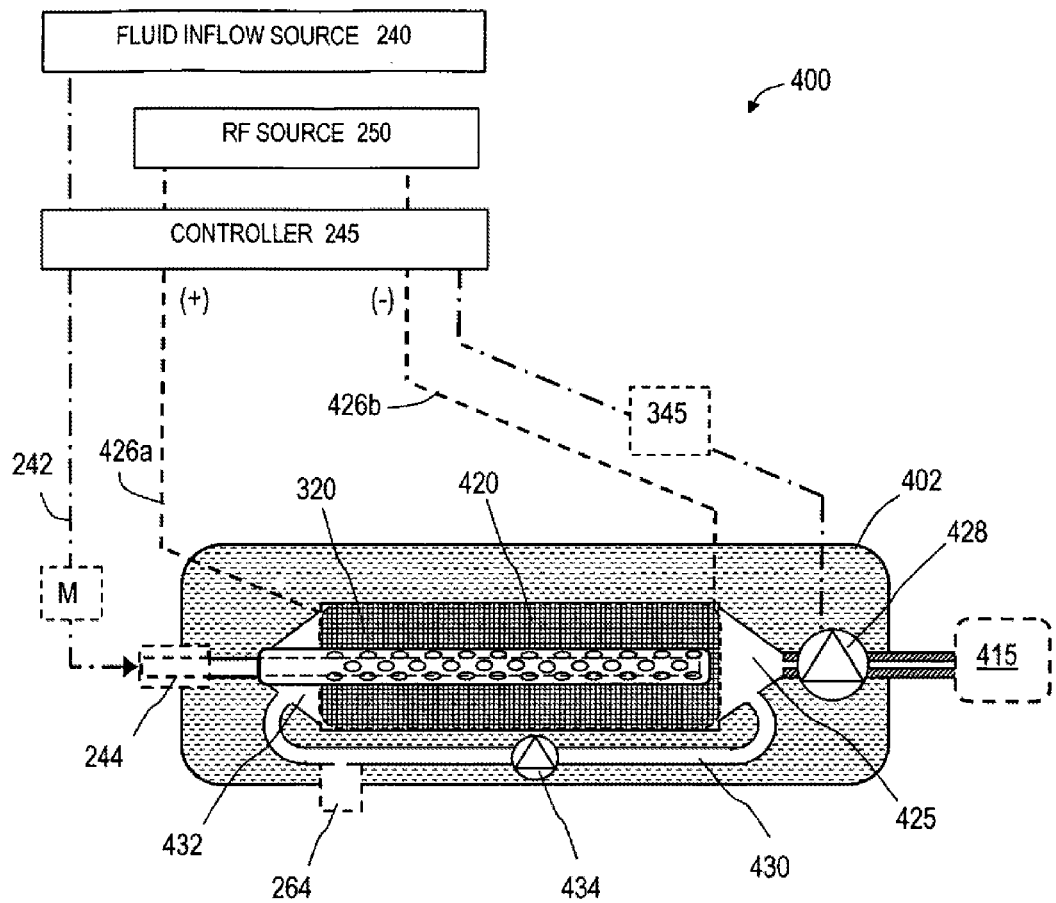
FIG. 11 is another embodiment similar to that of FIG. 7 with an alternative system for delivering thermal energy.

FIG. 11 illustrates another system embodiment 400 with handle 402 that utilizes a resistive element 420 in interior chamber 425 to cause the liquid-to-vapor phase change in the inflowing media M. All other system components are similar to the previous embodiments and have similar reference numbers. The electrical leads 426a and 426b in this embodiment are coupled to opposing ends of resistive element 420. In one embodiment, the resistive element 420 comprises a flow permeable structure such as a syntactic material or open-cell material (FIG. 11). The terms "syntactic", "open-cell" and "flow permeable" as used herein refer to any structure that has substantial porosity for allowing fluid flow therethrough. Such materials have the advantage of providing very high surface areas for conducting heat from an $I^2R$ heated material to pressurized media flows therein. The syntactic structure is further selected to provide an internal pore dimension that causes diffusion and atomization of high pressure inflows, for example of sterile water or saline. For example, the resistive element 420 can comprise a syntactic metal, resistive ceramic composite, or include a carbon portion. Such materials are available from ERG Materials and Aerospace Corp., 900 Stanford Avenue, Oakland, Calif. 94608 and Poco Graphite (http://www.poco.com). The open-cell material also can be an open cell foam that is metal plated, a sintered material, a plated entangled filament material, or any ordered or disordered structure commonly known in the art.

In the embodiment of FIG. 11, the system further includes a valve system 428 and recirculating channel 430 that are adapted for controlling the generation and release of vapor from working end 415. In the previous embodiments, the use of Rf energy delivery for vapor generation in chamber 225 (FIG. 7) can cause instantaneous high pressure flows of vapor. In the system embodiment of FIG. 11, the delivery of energy by means of resistive element 420 can require a fraction of a second or more to produce vapor from high pressure inflows of liquid media M. For this reason, the interior chamber 425 includes a recirculation channel 430 for a looped flow of vapor—or vapor and water droplets—that circulates back to inflow channel or the proximal end 432 of interior chamber 425. It should be appreciated that the recirculation channel 430 can be entirely housed in handle 402 or can circulate back to the source 245 or another intermediate chamber. The recirculation channel 430 also is operatively coupled to a pressure relief valve 262 as described above, and can further include a one-way valve indicated at 434. In operation of the embodiment, the system is actuated to create vapor which can circulate until a switch 435 coupled to controller 245 and valve 428 is actuated to release vapor M' from interior chamber 425. In all other respects, the method of the invention is the same as described above.

The schematic view of system 400 in FIG. 11 depicts the valve 428 in the handle, but the valve can also be located in working end 415 or elsewhere in introducer sleeve 205. Such valve systems can be linked to controller 245 by electrical leads in the introducer wall. In another embodiment, the valve 428 can be in the working end 415 and the recirculation channel 430 also can extend through the introducer sleeve 205 to the working end 415. This system thus assures that high quality vapor will be ejected from the working end.

The scope of the invention includes the use valve system 428 and recirculating channel 430 in other embodiments that utilize Rf, laser microwave or other energy deliver mechanisms. For example, in an Rf energy system as in FIG. 7, the valve and recirculating channel 430 systems can be used to control slight inconsistencies in vapor generation due to varied liquid inflow rates that sometimes results in sputtering and incomplete vaporization or inflowing media.

In another embodiment similar to that of FIG. 11, the system can infuse heated water (or saline or another liquid) from an external source under high pressure into an enclosed interior chamber of the system. The system also includes a valve similar to valve 428 in FIG. 11. Upon opening of the valve, the release of pressurized fluid will in part release the energy that was exerted on the fluid in the form of pressure—which will be converted into the energy required to vaporize the heated fluid. This type of system has the advantage of not requiring a thermal energy source with sufficient capacity for vaporizing needed volumes of vapor. Instead, a pressurization mechanism combined with a less robust thermal energy delivery system can be used to produce the required volume of vapor. Such sources can be external to the handle of the introducer.

The scope of the invention included use of the system to apply energy from a phase-change release to tissue for tissue modification in various procedures. The system can be configured with a needle-like working end to treat tumor tissue in a prostate, liver, kidney, breast, lung, vertebra and the like. The system can be configured with a needle-like working end for ablating fibroids. In another embodiment, a very small gauge needle (e.g., 36 ga.) can be used with fiber optic viewing to treat macular degeneration for shrinking and sealing leaking microvasculature. As very small gauge needle also can be used in a vision correction treatment to treat the cornea. A series of spots around the cornea can be targeted with vapor to shrink collagen to create a steepened cornea for treating presbyopia or to treat hyperopia. In another embodiment, the system can use a phase change energy release in an endometrial ablation procedure. In another embodiment, the system can use a small gauge blunt-tipped vapor delivery device that used pulses of vapor to cut brain tissue without causing any collateral thermal damage. A similar device can be used in orthopedic surgery to cut ligaments, cartilage and the like. The system can use in a cutting loop for TURP procedures. The system also can be used for delivering energy to a body lumen such as a blood vessel. In another embodiment, the system can be used to shrink lung tissue to cause lung volume reduction.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

What is claimed is:

1. A method of applying energy to soft tissue comprising:

generating a flow of vapor such that the vapor is ejected from a device in a flow of vapor;

generating a second flow of a second media and combining the second media with the vapor where the second media is depressurized; and introducing the flow of vapor to interfacing soft tissue wherein the vapor and second media deliver energy sufficient to modify the tissue.

2. The method of claim 1 wherein the introducing step includes the vapor undergoing a vapor-to-liquid phase transition thereby delivering thermal energy to the tissue.

3. The method of claim 1 wherein the introducing step includes injecting the vapor at a high velocity sufficient to deliver mechanical energy to the soft tissue.

4. The method of claim 1 further comprising controlling the parameters of the flow of vapor, the parameters selected from the group of the heat of vaporization of the vapor, the pressure of the flow of vapor, the volume of the flow of vapor and the duration of the flow of vapor.

5. The method of claim 1, where the second media comprises a media consisting of at least one of a liquid or a particulate matter and where generating the second flow media and combining the second flow media comprises reducing the mass average temperature of the flow of vapor.

6. The method of claim 1, wherein the second media comprises at least one of a depressurized $CO_2$, $N_2$, $O_2$ or $H_2O$.

7. A method as in claim 1 further comprising applying aspiration forces about the interface of the flow of vapor with the soft tissue.

8. The method of claim 1 wherein modifying tissue includes at least one of tissue ablation, obliteration, scouring and volumetric removal.

9. The method of claim 4 including controlling the parameters of the flow of vapor to obliterate a selected softer tissue while preventing obliteration of a selected harder tissue.

10. The method of claim 1 wherein the tissue includes at least one of disc tissue, adipose tissue, tumorous tissue and ocular tissue.

11. The method of claim 1 further comprising generating the flow of vapor by at least one of resistive heating means, radiofrequency (Rt) energy means, microwave energy means, photonic energy means, magnetic induction energy means, compression and decompression means, and ultrasonic energy means.

12. A method of applying energy to mammalian tissue comprising the steps of generating a flow of vapor, introducing a flow of vapor into an interface with tissue, and controlling the parameters of the flow for discriminating between first tissue and second adjacent tissues for volumetric removal of the first tissue without volumetric removal of the second tissue.

13. A method as in claim 12 further comprising applying aspiration forces about the interface of the flow of vapor with the tissue for extracting the tissue.

14. A method as in claim 12 wherein the first tissue is a less fibrous tissue and the second tissue is more fibrous tissue.

15. A method as in claim 12 wherein the first tissue is a disc nucleus portion and the second tissue is a disc annulus portion.

16. A method as in claim 12 wherein the first tissue is adipose tissue and the second tissue is non-adipose tissue.

17. A method as in claim 12 wherein the first tissue is less dense tissue and the second tissue is more dense tissue.

18. A method as in claim 12 wherein the first tissue is soft tissue and the second tissue is vascular tissue.

19. A method as in claim 12 wherein the first tissue is tumorous tissue and the second tissue is non-tumorous tissue.

20. A surgical system for applying energy to tissue, the system comprising:
a probe having a handle end that extends to a working end;
a source of a vaporized fluid media that communicates with at least one vapor outlet in the working end;
a negative pressure source that communicates with at least one aspiration port in the working end
where the vapor outlet and aspiration port are recessed in the working end and the at least one vapor outlet is directed toward the at least one aspiration port.

21. The surgical system of claim 20 wherein the at least one aspiration port has an open cross-section that is substantially larger than the open cross-section of the at least one vapor outlet.

22. The surgical system of claim 20 further including an element that is extendable from the working end and a rotation mechanism for rotating the working end, where the element is adapted to mechanically cut or scour tissue.

23. The surgical system of claim 20 further comprising a controller for controlling at least on of the pressure of the source of a vaporized fluid media and the pressure of the negative pressure source.

24. The surgical system of claim 20 further comprising a MEMS sensor in the working end.

25. The method of claim 1 wherein the second media allows for controlling the average mass temperature of the vapor.

26. The method of claim 1 wherein the second media is introduced into the vapor to reduce the mass average temperature of the vapor.

27. The method of claim 20, where the vapor outlet and aspiration port are arranged in a concentric configuration within the working end.

28. The method of claim 20, where the vapor outlet and aspiration port are positioned in opposition to each other in the working end.

29. A surgical system for applying energy to tissue,
a probe having a handle end that extends to a working end;
a source of a vaporized fluid media that communicates with at least one vapor outlet in the working end;
a negative pressure source that communicates with at least one aspiration port in the working end; and
an extendable cutting loop extendable from the working end and a rotation mechanism for rotating the working end.

30. The surgical system of claim 29 wherein the at least one vapor outlet is directed toward the at least one aspiration port.

31. The surgical system of claim 29 wherein the at least one vapor outlet is in a recessed portion of the working end.

32. The surgical system of claim 29 wherein at least one aspiration port is in a recessed portion of the working end.

33. The surgical system of claim 29 wherein the at least one aspiration port has an open cross-section that is substantially larger than the open cross-section of the at least one vapor outlet.

34. The surgical system of claim 29 further comprising a controller for controlling at least on of the pressure of the source of a vaporized fluid media and the pressure of the negative pressure source.

35. The surgical system of claim 29 further comprising a MEMS sensor in the working end.

36. A method of applying energy to soft tissue comprising:
generating a flow of vapor such that the vapor is ejected from a device in a flow of vapor;
generating a second flow of a second media and combining the second media with the vapor where the second media comprises a liquid or a particulate substance; and
introducing the flow of vapor to interfacing soft tissue wherein the vapor and second media deliver energy sufficient to modify the tissue.

* * * * *